US009187537B2

(12) United States Patent
Cha et al.

(10) Patent No.: US 9,187,537 B2
(45) Date of Patent: Nov. 17, 2015

(54) RECOMBINANT SILK PROTEIN DERIVED FROM SEA ANEMONES, METHOD FOR MANUFACTURING SAME, AND COMPOSITION FOR MANUFACTURING SILK FIBERS INCLUDING SAME

(75) Inventors: Hyung Joon Cha, Phohang-si (KR); Yun Jung Yang, Seoul (KR); Yoo Seong Choi, Seoul (KR)

(73) Assignee: POSTECH ACADEMY-INDUSTRY FOUNDATION POHANG UNIVERSITY OF SCIENCE AND TECHNOLOGY, Pohang-Si, Gyeongsangbuk-Do (KR)

( * ) Notice: Subject to any disclaimer, the term of this patent is extended or adjusted under 35 U.S.C. 154(b) by 105 days.

(21) Appl. No.: 14/004,658

(22) PCT Filed: Feb. 6, 2012

(86) PCT No.: PCT/KR2012/000855
§ 371 (c)(1),
(2), (4) Date: Sep. 11, 2013

(87) PCT Pub. No.: WO2012/124896
PCT Pub. Date: Sep. 20, 2012

(65) Prior Publication Data
US 2015/0057435 A1 Feb. 26, 2015

(30) Foreign Application Priority Data

Mar. 11, 2011 (KR) ........................ 10-2011-0021741
Jan. 6, 2012 (KR) ........................ 10-2012-0002161

(51) Int. Cl.
| C07K 14/435 | (2006.01) |
| D01F 4/00 | (2006.01) |
| D01D 5/00 | (2006.01) |
| D01D 5/06 | (2006.01) |

(52) U.S. Cl.
CPC ..... *C07K 14/43504* (2013.01); *C07K 14/43595* (2013.01); *D01D 5/0007* (2013.01); *D01D 5/06* (2013.01); *D01F 4/00* (2013.01); *D10B 2211/04* (2013.01)

(58) Field of Classification Search
None
See application file for complete search history.

(56) References Cited

U.S. PATENT DOCUMENTS

| 4,059,694 | A | 11/1977 | Norton et al. |
| 2005/0260706 | A1* | 11/2005 | Kaplan et al. ............... 435/69.1 |

OTHER PUBLICATIONS

Putnam et al., "Sea Anemone Genome Reveals Ancestral Eumetazoan Gene Repertoire and Genomic Organization", Science, 2007, 317:86-94. DOI: 10.1126/science.1139158.*
Teulé et al., "A protocol for the production of recombinant spider silk-like proteins for artificial fiber spinning", Nature Protocols, 2009, 4(3):341-355.*
Xia et al., "Native-sized recombinant spider silk protein produced in metabolically engineered *Escherichia coli* results in a strong fiber", PNAS, 2010, 107(32):14059-14063.*
Bornhurst et al., "Purification of Proteins Using Polyhistidine Affinity Tags", Methods in Enzymology, 2000, vol. 326, pp. 245-254.*
Office Action dated Jan. 20, 2015 of corresponding Japanese Patent Application No. 2013-558776—5 pages.
Bandmann et al., "Combinatorial expression vector engineering for tuning of recombinant protein production in *Escherichia coli*", Nucleic Acids Research, 2007, vol. 35, No. 5, e32—15 pages.
Yang et al., "Sea Anemone Protein for a Novel Silk Material", Abstracts of The Korean Society for Microbiology and Biotechnology 2011 International Symposium & Annual Meeting [online], p. 317, B-24.
Bishop et al.,"Cerianthin: A silk-like protein from sea anemones", Federation Proceedings, 1978, vol. 37, p. 1528, 1422.
Database UniProt, "Predicted protein", XP002727749, Database accession No. A7T4X7, Oct. 2, 2007—1 page.
Guy Naamati et al, "Expansion of tandem repeats in sea anemone *Nematostella vectensis* proteome: A source for gene novelty?", BMC Genomics, Jan. 1, 2009, vol. 10:593, No. 1, pp. 1-17.
Yun Jung Yang et al, "Production of a novel silk-like protein from sea anemone and fabrication of wet-spun and electrospun marine-derived silk fibers", NPG Asia Materials, Jun. 1, 2013, vol. 5, pp. 1-7.
Extended European Search Report dated Aug. 6, 2014 of corresponding European Patent Application No. 12758020.7—6 pages.
Hyung Joon Cha, "Development of marine organism derived-silk protein materials", Final Report, R&D/ 2009-0175, Korea Institute of Marine Science & Technology Promotion, The Ministry of Land, Transport and Maritime Affairs, Sep. 9, 2011 in 66 pages. English translation of Summary and Content is provided at pp. 7-10.
Yun Jung Yang et al., "Increased repeats of recombinant silk-like protein derived from sea anemone affects its mechanical properties", 2011 The Korean Society for Biotechnology and Bioengineering ("KSBB") Fall meeting and International Symposium pp. 187, Oct. 2011 (poster presentation on Oct. 5, 2011).
Hyung Joon Cha et al., "Nanoscale enzyme reactors of organophosphorous hydrolase in mesoporous carbons for reliable and sensitive detection of organophosphate nerve agents", Proceedings of The Korean Institute of Chemical Engineers ("KIChE" ) Fall meeting and Symposium, pp. 170, Oct. 2011 (poster presentation on Oct. 26, 2011).

(Continued)

*Primary Examiner* — Suzanne M Noakes
(74) *Attorney, Agent, or Firm* — Knobbe, Martens, Olson & Bear, LLP

(57) ABSTRACT

There are provided a recombinant silk protein derived from sea anemones, a method for producing the same, and a composition for preparing a silk fiber including same. The recombinant silk protein derived from sea anemones has sequence features similar to genetic information of a silk protein derived from spiders and silkworms. Also, a large amount of recombinant silk protein derived from sea anemones may be produced from a transformant and it has good physical properties such as strength and elasticity. Therefore, the recombinant silk protein derived from sea anemones can be usefully applied in various industrial fields in which natural silk protein can be applied, and it is expected to create new industrial fields based on its distinctive mechanical properties.

10 Claims, 15 Drawing Sheets

(56) References Cited

OTHER PUBLICATIONS

Yun Jung Yang et al., "Investigation on sea anemone protein as a novel silk material", Proceedings of The Korean Institute of Chemical Engineers ("KIChE") Spring meeting and Symposium, pp. 173, Apr. 27, 2011.

Yun Jung Yang et al., "Sea anemone protein for a novel silk material", 2011 international Symposium & Annual Meeting organized by The Korean Society for Microbiology and Biotechnology, pp. 239, Jun. 22, 2011.

Yun Jung Yang et al., "Recombinant Silk-like Protein Derived from Sea Anemone as a Novel Silk Biomaterial", Poster Presentation, Proceedings of the 3rd Asian Biomaterials Congress organized by the Korean Society for Biomaterials, Sep. 15, 2011.

NCBI, GenBank accession No. XP_001621085.1, Feb. 13, 2008.

Kristensen et al., "Oxic and anoxic decomposition of tubes from the burrowing sea anemone *Ceriantheopsis americanus*: Implications for bulk sediment carbon and nitrogen balance" Journal of Marine Research, 1991, vol. 49, pp. 589-617.

Yang et al, "Marine silk protein from sea anemone" in: AIChE 2011 annual meeting, Minneapolis, Oct. 19, 2011.

International Search Report dated Aug. 9, 2012 of PCT/KR2012/000855 which is the parent application—2 pages.

\* cited by examiner

FIG. 3
(1)
# (30kDa)
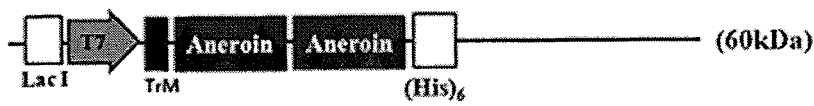# (60kDa)
# (90kDa)
# (120kDa)
(2)
# (30kDa)
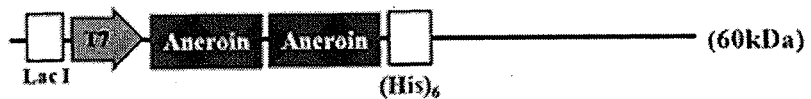# (60kDa)
# (90kDa)
# (120kDa)
(1) schematic diagram of expression system repeating genes of sea anemone silk protein with expression-enhanced motif twice, three times, and four times;
(2) schematic diagram of expression system repeating genes of sea anemone silk protein twice, three times, and four times;

FIG. 7
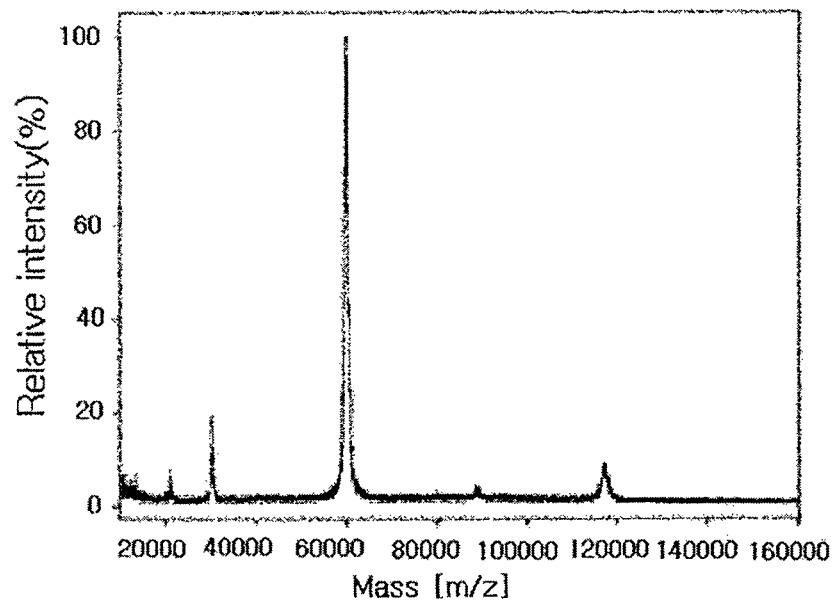
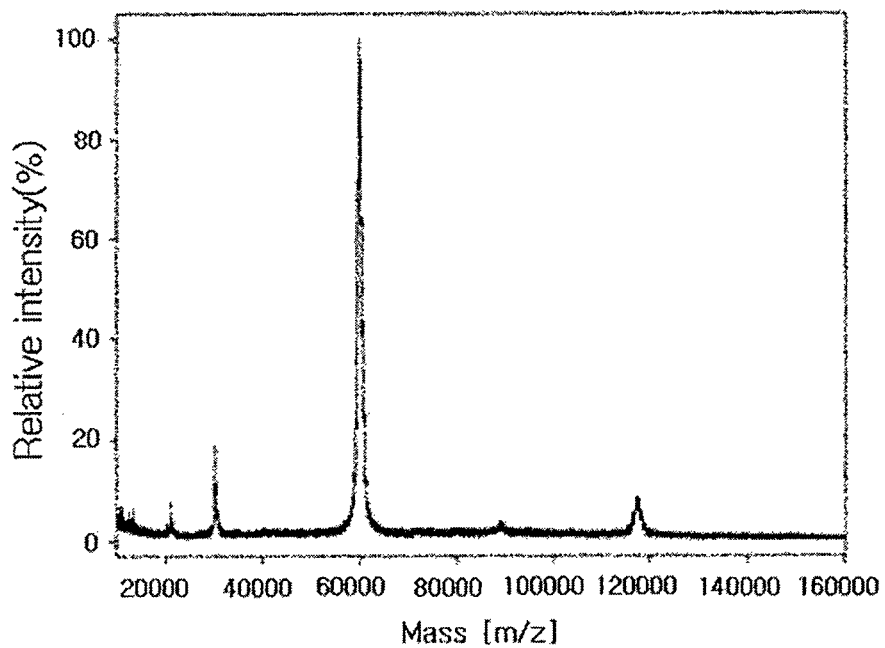

FIG. 10
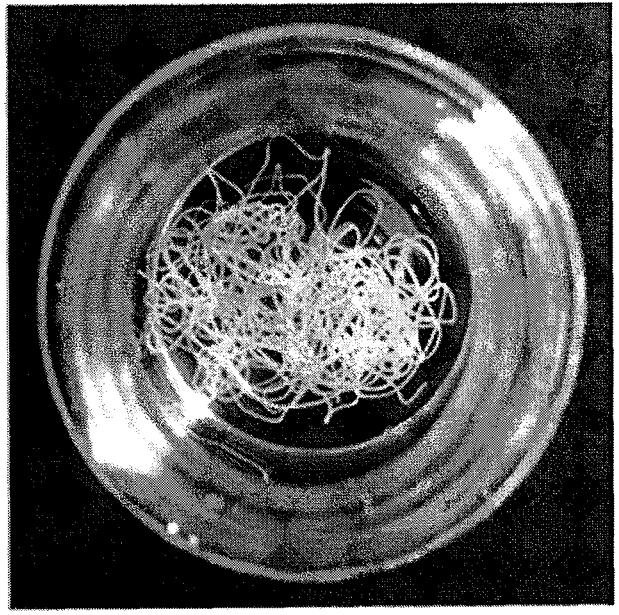

FIG. 12
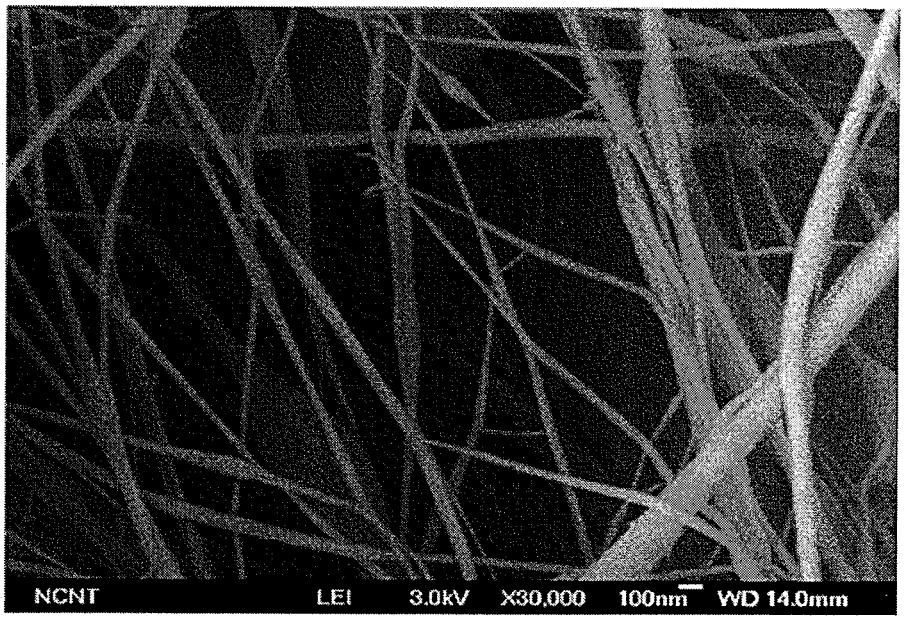
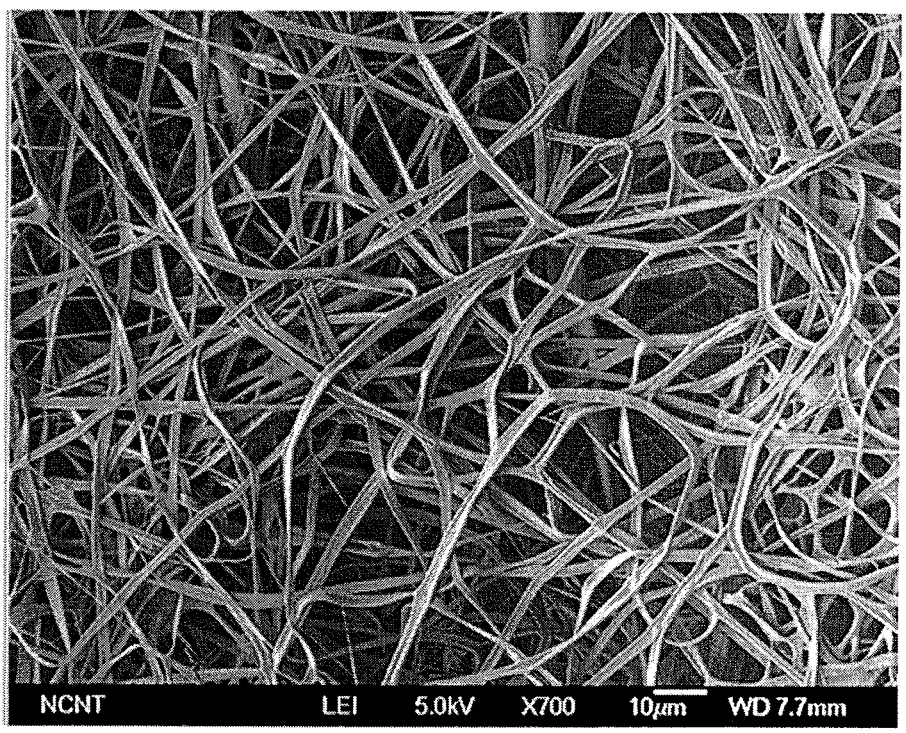

RECOMBINANT SILK PROTEIN DERIVED FROM SEA ANEMONES, METHOD FOR MANUFACTURING SAME, AND COMPOSITION FOR MANUFACTURING SILK FIBERS INCLUDING SAME

BACKGROUND

1. Field of the Invention

The present invention relates to a recombinant silk protein derived from sea anemones, a method for producing the same, and a composition for preparing a silk fiber including same.

2. Discussion of Related Art

Natural silk protein materials have been used as general materials for clothes for a long period of time, and may also be used as next-generation highly functional industrial materials because natural silk proteins have good biocompatibility, superior elasticity, and physical strength, and are capable of being formed into various forms such as powder, a membrane, a porous body, or gel, and can be chemically modified from natural proteins.

It known that the silk proteins have so far mainly been produced by silkworms and spiders.

In the case of silkworm silk protein, conventional production of textiles in which silkworms can be raised and 5 kg of silk protein can be produced from about 1,500,000 of silkworms in an area of 300 $m^2$ has been widely used. Further, the natural silkworm silk protein may be used for cosmetic materials, an enzyme immobilization support, materials for cell cultures, or industrial materials such as artificial skin, because it is a human-friendly material which does not cause immunoreaction or allergic reaction. However, there is a minor limitation in using the silkworm silk protein for industrial materials because it has insufficient durability, that is, strength. Thus, various studies aimed at improving physical properties of the silkworm silk protein is underway. For example, there is research aimed at separating silk fibroin, a major component of silkworm silk protein, based on molecular weight, and a function thereof, research into preparation of a fine body of silkworm silk protein and skin affinity thereof, research aimed at improving physical properties through blending of a silkworm silk protein and a chemical synthetic polymer, and research into mixing a silkworm silk protein and a natural glucose-based polymer compound.

In the case of spider silk protein, since natural spider silk protein was found to have very good physical properties such as durability and elasticity, research into using the spider silk protein as industrial materials has been performed actively. However, it is known that it is impossible to raise spiders because they eat each other, and it is impossible to separate and produce natural silk protein like silkworm silk protein because the amount of silk protein produced from spiders is very small. Therefore, much research into spider silk protein has focused on introducing genes of the spider silk protein to various protein expression systems to produce a recombinant protein, and much effort has been attempted to perform mass production of a spider silk protein in E-coli, yeast, plant cells, animal cells, a gene-transplanted animal, or the like. On the whole, due to intensive research and investment since 2000, research into spider silk protein has recently begun to bear fruit, but genes of spider silk protein include repeated DNA sequences and repeated specific amino acid sequences such as glycine, alanine, or serine, which results in difficulty in producing natural silk protein materials by recombination. Even when the spider silk protein whose specific sequence is only partially expressed is mass produced, the produced material may be made into the form of yarn, but the physical properties are largely insufficient compared to those of natural spider silk protein.

Therefore, based on an understanding of the generic properties and physical properties of natural silkworm and spider silk protein, methods for mass production of a protein with such sequence features have been studied. Further, much effort has been made to search for new natural silk protein materials and secure an original patent thereof. From such a viewpoint, it is reported that ant and bee silk proteins have gene sequence features similar to silkworm or spider silk protein, and new silk protein materials in which genes with properties of a natural silk protein are redesigned are being designed.

Meanwhile, sea anemone is the general name of an animal of order Actiniaria which belongs in Cnidaria, phylum Cnidaria, class Anthozoa. Some sea anemones may dwell in the sea and attach to reef, but others may dwell in the sand or move using a pedal disc. Further, the sea anemone may float through a pedal disc having a column shape or swim by moving its body or tentacles. The sea anemone may eat floating planktons or even a larger fish. The sea anemone captures prey using many cnidocytes on tentacles in which toxic materials such as tetramin are discharged. Types of sea anemone include red rock anemone, coral anemone, or the like. The body includes an open mouth in the middle and several tentacles which are flexible muscle, cylindrical, and hollow. The body has a length of 1.5 to 5 cm and various widths. The color of the body is white, green, blue, orange, red, or the like. Most sea anemones are dioecious and reproduce sexually. Also, most sea anemones have external fertilization, but some species are ovoviviparous. Up to now, about 1,000 species of the sea anemone are known worldwide, and they each dwell independently without forming a colony, which is characteristically different from other animals that belong to class Anthozoa.

Species dwelling in the sea have not been investigated on the level of genes and proteins, and thus research into production of silk protein from these species has been almost non-existent. Therefore, when a method of producing a recombinant silk protein from many sea anemones dwelling in the sea is studied, it is thought that the recombinant silk protein may be substituted for silk protein derived from spiders and silkworms in the related art. Therefore, there is need for development of a recombinant silk protein derived from sea anemones.

SUMMARY OF THE INVENTION

The present inventors analyzed sequences of silk proteins derived from spiders and silkworms known in the related art and obtained new genetic information with the same sequence features as these sequences from sea anemones. Also, they found that when a recombinant silk protein derived from sea anemones is expressed and purified through a transformant, the resultant recombinant silk protein derived from sea anemones can be wet-spun or electrically spun to obtain a silk fiber material that has good strength and elasticity. On this basis, they completed the present invention.

According to an aspect of the present invention, there are provided a recombinant silk protein derived from sea anemones, a method for producing the same, and a composition for preparing a silk fiber including same.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which:

FIG. 3 is a schematic diagram of expression systems of genes of sea anemone silk proteins coding silk proteins having sizes of 60 kDa, 90 kDa, and 120 kDa produced by repeating genes of a sea anemone silk protein twice, three times, and four times;

FIG. 7 shows mass analysis results of purified recombinant silk proteins derived from sea anemones having sizes of 30 kDa and 60 kDa, obtained using MALDI-MS analysis;

FIG. 10 shows a silk fiber containing a recombinant silk protein derived from sea anemones obtained after wet spinning;

FIG. 12 shows a silk fiber containing a recombinant silk protein derived from sea anemones obtained after electric spinning, observed by scanning electron micrograph, (a) electric spinning using phosphoric acid, (b) electric spinning using formic acid;

DETAILED DESCRIPTION OF EXEMPLARY EMBODIMENTS

Figure 1:
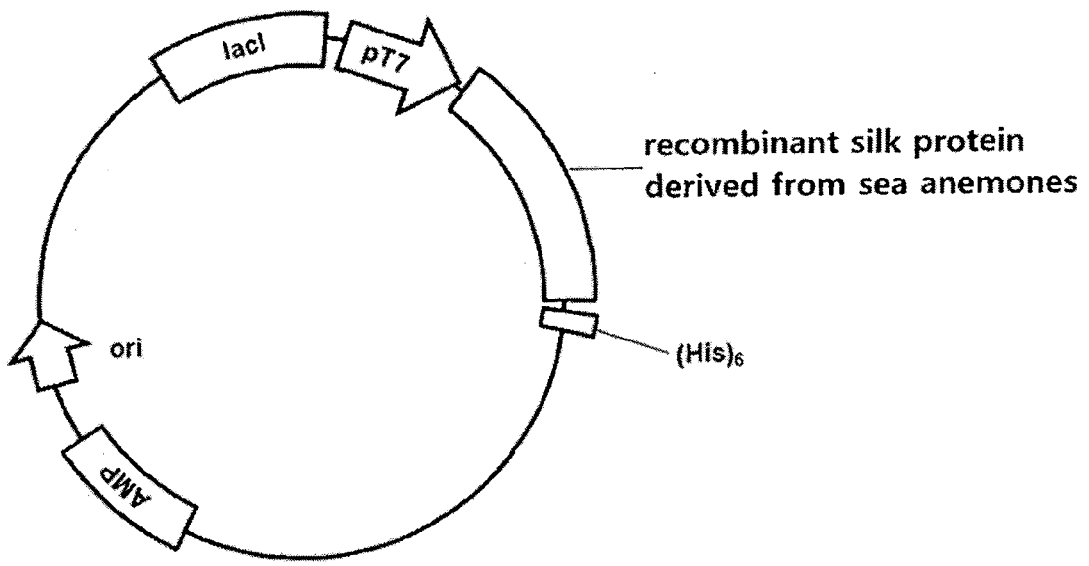
FIG. 1 is a schematic diagram of an expression vector including genes of a sea anemone silk protein.

According to the present invention, there is provided a recombinant silk protein derived from sea anemones including an amino acid sequence of SEQ ID NO. 2 or 3.

Further, according to the present invention, there is provided a recombinant silk protein derived from sea anemones having at least 80% sequence homology to an amino acid sequence of SEQ ID NO. 2 or 3. Preferably, according to the present invention, there is provided a recombinant silk protein derived from sea anemones having at least 90% sequence homology to an amino acid sequence of SEQ ID NO. 2 or 3.

Further, according to the present invention, there is provided a method of producing a recombinant silk protein derived from sea anemones including:

1) preparing an expression vector including genes of a sea anemone silk protein coding an amino acid sequence of SEQ ID NO. 1, 2) inserting the expression vector into a host cell to prepare a transformant, 3) producing a recombinant silk protein derived from sea anemones from the transformant, and 4) separating and purifying the produced recombinant silk protein derived from sea anemones.

Further, according to the present invention, there is provided a method of producing a recombinant silk protein derived from sea anemones including:

1) preparing an expression vector including genes of a sea anemone silk protein coding an amino acid sequence having at least 80% sequence homology to an amino acid sequence of SEQ ID NO. 1, and preferably at least 90% sequence homology, 2) inserting the expression vector into a host cell to prepare a transformant, 3) producing a recombinant silk protein derived from sea anemones from the transformant, and 4) separating and purifying the produced recombinant silk protein derived from sea anemones.

Further, according to the present invention, there is provided a composition for preparing a silk fiber including at least one amino acid sequence selected from the group consisting of amino acid sequences of SEQ ID NOs. 2, 3 and 4.

Further, according to the present invention, there is provided a method of producing a silk fiber including:

1) preparing an expression vector including genes of a sea anemone silk protein coding an amino acid sequence of SEQ ID NO. 1, 2) inserting the expression vector into a host cell to prepare a transformant, 3) producing a recombinant silk protein derived from sea anemones from the transformant, 4) separating and purifying the produced recombinant silk protein derived from sea anemones, and 5) wet-spinning the purified recombinant silk protein derived from sea anemones.

Further, according to the present invention, there is provided a method of producing a silk fiber including:

1) preparing an expression vector including genes of a sea anemone silk protein coding an amino acid sequence having at least 80% sequence homology to an amino acid sequence of SEQ ID NO. 1, and preferably at least 90% sequence homology, 2) inserting the expression vector into a host cell to prepare a transformant, 3) producing a recombinant silk protein derived from sea anemones from the transformant, 4) separating and purifying the produced recombinant silk protein derived from sea anemones, and 5) wet-spinning the purified recombinant silk protein derived from sea anemones.

Further, according to the present invention, there is provided a method of producing a silk fiber including:

1) preparing an expression vector including genes of a sea anemone silk protein coding an amino acid sequence of SEQ ID NO. 1, 2) inserting the expression vector into a host cell to prepare a transformant, 3) producing a recombinant silk protein derived from sea anemones from the transformant, 4) separating and purifying the produced recombinant silk protein derived from sea anemones, and 5) electric-spinning the purified recombinant silk protein derived from sea anemones.

Further, according to the present invention, there is provided a method of producing a silk fiber including:

1) preparing an expression vector including genes of a sea anemone silk protein coding an amino acid sequence having at least 80% sequence homology to an amino acid sequence of SEQ ID NO. 1, and preferably at least 90% sequence homology, 2) inserting the expression vector into a host cell to prepare a transformant, 3) producing a recombinant silk protein derived from sea anemones from the transformant, 4) separating and purifying the produced recombinant silk protein derived from sea anemones, and 5) electric-spinning the purified recombinant silk protein derived from sea anemones.

Further, according to the present invention, there is provided a silk fiber produced by a method of producing the silk fiber.

Hereinafter, the present invention will be described in detail.

According to the present invention, a portion of a codon sequence in the mRNA sequence of a sea anemone silk protein coding an amino acid sequence of SEQ ID NO.1 is rearranged so as to be optimized, an expression vector including genes of the optimized sea anemone silk protein is prepared, the expression vector is inserted into a host cell to prepare a transformant, and then the recombinant silk protein derived from sea anemones is produced from the transformant.

The produced recombinant silk protein derived from sea anemones has an amino acid sequence of SEQ ID NO. 2, 3 or 4, the amino acid sequence of SEQ ID NO. 2 includes six histidines (6×his purification tag sequence; HHHHHH—SEQ ID NO. 5) connected to C-terminal of the amino acid sequence of SEQ ID NO. 1, the amino acid sequence of SEQ ID NO. 3 includes six histidines connected to C-terminal of the amino acid sequence of SEQ ID NO. 1 and an expression-enhanced motif sequence (MKAIFVLKDDDDK; SEQ ID NO. 6) connected to N-terminal, and the amino acid sequence of SEQ ID NO. 4 includes ten amino acid sequences or modified amino acid sequences thereof. The produced recombinant silk protein derived from sea anemones may be a polypeptide in which at least one amino acid sequence of SEQ ID NO. 4 are connected to each other, a polypeptide in which 1 to 200 of amino acid sequences are connected to each other, and more preferably, a polypeptide in which 1 to 120 amino acid sequences are connected to each other. Further, the produced recombinant silk protein may be a polypeptide in which other amino acid sequences are connected to each other in 1 to 200 or 1 to 120 amino acid sequences.

The natural sea anemone silk protein (i.e., aneroin) includes a repetitive structure of five amino acids [GPGXX (X=A,V,S,Y); SEQ ID NO. 7] as in a silk protein (i.e., flageliform) derived from spiders in the related art, and an amino acid sequence (amino acid sequence of SEQ ID NO.1) similar thereto, which is set out in information of NCBI Reference Sequence (XP_001621085.1). The sea anemone silk protein obtained through NCBI search has 49.5% identity and 60.2% homology to silk protein derived from *Bombyx mori*, and 43.2% identity and 64% homology to silk protein derived from *Nephila clavipes*.

The recombinant silk protein derived from sea anemones according to the present invention may be mass-produced by a genetic engineering method because foreign genes may be inserted into conventional vectors to be expressed. Hereinafter, a method of producing the recombinant silk protein derived from sea anemones according to the present invention will be described in detail.

First, the sea anemone silk protein is optimized by rearranging a portion of a codon sequence in an mRNA sequence. The DNA sequence of the sea anemone silk protein may be modified into a codon which is mainly used in a host cell or another codon sequence in order to prevent duplication and repetition of a DNA codon sequence. DNA of the optimized sea anemone silk protein is added to restriction enzyme sites, Nde1 and Xho1, at both ends, followed by cloning into an expression vector, pET23b(+), including an expression promoter, T7 (pT7), thus preparing an expression vector. The resultant expression vector is allowed to include a histidine tag [6×his purification tag sequence; HHHHHH—SEQ ID NO: 5] at C-terminal, and a TrpL motif is introduced to N-terminal of the sea anemone silk protein in order to increase the amount of sea anemone silk protein to be expressed [expression-enhanced motif sequence; MKAIFVLKDDDDK—SEQ ID NO. 6]. The expression vector may be suitably selected or prepared depending on types and properties of a host cell for producing a protein.

A method of inserting the expression vector into a host cell to prepare a transformant or producing a recombinant protein from a transformant may be easily performed using a conventional method. Examples of the host cell used for the present invention include *E-coli*, yeast, animal cells, plant cells, insect cells, or the like, but are not limited thereto. Hereinafter, a method of preparing a transformant using *E-coli* as the host cell to produce the recombinant silk protein derived from sea anemones from the transformant will be described in detail.

The prepared expression vector is inserted into a host cell by a heat shocking method of standing for 2 minutes at 42° C. to prepare a transformant, which produces a recombinant silk protein derived from sea anemones.

The transformant is inoculated onto an LB medium, preferably an LB medium containing ampicillin, followed by shaking. In order to induce expression of the recombinant silk protein derived from sea anemones, when the absorbance ($OD_{600}$) of a culture medium is 0.4 to 1.0 at 600 nm, preferably 0.8 to 0.9, a protein expression inducing material, isopropyl-β-D-thiogalactopyranoside (IPTG), is added thereto in an amount of 0.1 to 10 mM, followed by shaking for 3 to 24 hours at a temperature of 16 to 37° C. The cultured cells are centrifuged to remove a supernatant, recovered, and then the recovered cells are floated in a lysis buffer, and broken using a sonicator or a homogenizer. A portion of the broken cells are separated into a whole cell lysate, a soluble fraction, and an insoluble fraction, and then the remaining whole cell lysate is centrifuged to recover a supernatant. The recombinant silk protein derived from sea anemones expressed in the soluble fraction is separated and purified from the recovered supernatant using a his-tag column. Respective fragments are diluted in a SDS-PAGE buffer (0.5M Tris-HCl (pH 6.8), 10% glycerol, 5% SDS, 5% β-mercaptoethanol, 0.25% bromophenol blue), boiled and denatured for 5 minutes or more at 100° C., separated according to molecular weight by SPS-PAGE in SDS-polyacrylamide gel, and then expression of the recombinant silk protein from sea anemones is identified through western blot.

Subsequently, the recombinant silk protein derived from sea anemones produced in the host cell is subjected to affinity chromatography using a column filled with nickel resin, and thus proteins bonded to the column are purified in 40 mM to 5 M imidazol. Preferably, the soluble fragment of the broken cells including the recombinant silk protein derived from sea anemones is injected into a nickel-nitrilotriacetic acid (NTA) column, protein which is not boned to the column is washed using a washing solution (50 mM NaH$_2$PO$_4$, 300 mM NaCl, 30 mM imidazol, pH 8.0), and the protein is separated and purified from the column using an elution buffer (50 mM NaH$_2$PO$_4$, 300 mM NaCl, 300 mM imidazol, pH 8.0).

Further, the recombinant silk protein derived from sea anemones may be purified through thermal shocking and acid extraction. Preferably, the soluble fragment of the broken cells including the recombinant silk protein derived from sea anemones is subjected to thermal shocking at a temperature of 40 to 100° C. At this time, the produced insoluble fragment is separated by centrifugation, and the separated insoluble fragment is dissolved in an acid solution (for example, phosphoric acid, formic acid, or the like) to extract the recombinant silk protein derived from sea anemones.

From the recombinant silk protein derived from sea anemones purified through affinity chromatography, or thermal shocking and acid extraction, components other than water and protein in an aqueous protein solution are removed through dialysis using water, and finally powdery, purified recombinant silk protein derived from sea anemones is obtained through freeze-drying. The produced recombinant silk protein derived from sea anemones includes an amino acid sequence of SEQ ID NO. 2 or 3.

Generally, the sea anemone silk protein has a size of about 30 kDa, and the recombinant silk protein derived from sea anemones includes a large amount of proteins which are found at a position of not 30 kDa but 60 kDa or more when it is subjected to SDS-PAGE. It is thought that particles are hardly moved at the time of SDS-PAGE due to sequence features of amino acids of the recombinant silk protein derived from sea anemones. The same phenomenon has been found even when the silk proteins obtained from silkworms or spiders are subjected to SDS-PAGE. Therefore, the recombinant silk protein derived from sea anemones is subjected to MALDI-MS analysis in order to measure a correct size, and thus it is found that the molecular weight is present around 30 kDa. Further, when composition of amino acid of the recombinant silk protein derived from sea anemones which is predictable through calculation is compared to that of the recombinant silk protein derived from sea anemones which has been practically purified, purification of the recombinant silk protein derived from sea anemones may be found more clearly.

Further, according to the present invention, there is provided a composition for preparing a silk fiber including at least one amino acid sequence selected from the group consisting of amino acid sequences of SEQ ID Nos. 2, 3 and 4.

In the recombinant silk protein derived from sea anemones, the amino acid sequence of SEQ ID NO. 2 includes six histidines (6×his purification tag sequence; HHHHHH—SEQ ID NO. 5) connected to C-terminal of the amino acid sequence of SEQ ID NO. 1, the amino acid sequence of SEQ ID NO. 3 includes six histidines connected to C-terminal of the amino acid sequence of SEQ ID NO. 1 and an expression-enhanced motif sequence (MKAIFVLKDDDDK; SEQ ID NO. 6) connected to N-terminal, and the amino acid sequence of SEQ ID NO. 4 includes ten amino acid sequences or modified amino acid sequences thereof.

Further, according to the present invention, there is provided a composition for preparing a silk fiber including a polypeptide in which 1 to 200 of amino acid sequences of SEQ ID NO. 4 are connected to each other. Further, the produced recombinant silk protein may be a polypeptide in which other amino acid sequences are connected to each other in 1 to 200 or 1 to 120 amino acid sequences.

The silk fiber according to the present invention may be prepared by the recombinant silk protein derived from sea anemones using wet spinning or electric spinning.

Specifically, the powdery, purified recombinant silk protein derived from sea anemones is dissolved in (1) an acid solvent or an organic solvent, or a mixed solvent thereof; or (2) an acid solvent or an organic solvent, a mixed solvent thereof, in which at least one selected from the group consisting of urea, LiBr, N-methylmorpholine-N-oxide (NMMO), and zolium chrolide is dissolved.

Examples of the acid solvent include phosphoric acid, acetic acid, formic acid, hydrochloric acid, sulfuric acid, nitric acid, or the like, but are not limited thereto. Examples of the organic solvent include hexafluoroisopropanol (HFIP), hexafluoropropanol (HFP), hexafluoroacetone (HFA), trifluoroacetic acid (TFA), methylimidazolium chloride, or the like, but are not limited thereto. In the present invention, HFIP is preferable. In this case, the recombinant silk protein derived from sea anemones which is dissolved in the solvent has a concentration of 3 to 25% (w/v), and preferably 5 to 15% (w/v). When the concentration of the recombinant silk protein derived from sea anemones is outside of the range, wet spinning or electric spinning may not occur.

When a silk fiber is prepared using wet spinning, the recombinant silk protein derived from sea anemones which is dissolved in the solvent is wet-spun at a rate of 0.5 to 20 mL/hr, and preferably 10 mL/hr, in a coagulation bath including a coagulation-inducing solvent. Examples of the coagulation-inducing solvent include methanol, isopropanol, acetone, ammonium sulfate, water, or the like, but are not limited thereto. In the present invention, methanol and isopropanol are preferable, and a solvent of mixed methanol and isopropanol in a volume ratio of 1:1 is more preferable. A silk fiber in the form of intact and homogeneous yarn and having a homogeneous diameter of 30 to 120 µm, preferably 40 to 80 µm, may be obtained by wet spinning.

The obtained silk fiber in the form of yarn is kept for several minutes to hours in a coagulation-inducing solvent. This is a post-spinning process which affects physical properties of fiber yarn, which is an important process. In other words, the obtained silk fiber in the form of yarn is kept in various coagulation-inducing solvents, and thereby physical properties of the fiber may be improved. Preferably, a solvent is changed twice to seven times at intervals of 10 minutes to 30 minutes. In this case, at least one selected from the group consisting of DMSO, $H_2O_2$, calcium phosphate, potassium ferricyanide, and glutaraldehyde may be added as a cross-linking agent to the solvent, and thus change of physical properties of protein may be induced. Preferably, 10% (v/v) to 60% (v/v) of DMSO, and more preferably 20% of DMSO, may be added. After the post-spinning process, the obtained fiber yarn may be selectively drawn, preferably to 1.5 to 10 times the original length, and more preferably to twice the length. When the silk fiber containing the recombinant silk protein derived from sea anemones obtained through wet spinning is observed by optical microscope and scanning electron microscope, it may be found that the silk fiber has a homogeneous diameter and is formed of intact protein. Finally, the wet span silk fiber is kept after a drying process. Also, a stress-strain curve may be obtained using a nano Universal Testing Machine (UTM).

Further, when a silk fiber is prepared using an electric spinning method, acetic acid may be added to the recombinant silk protein derived from sea anemones dissolved in the solvent. Here, the acetic acid preferably corresponds to 5 to 10 volume % of the recombinant silk protein solution derived from sea anemones. This is followed by performing electric spinning at a voltage of 10 to 20 kV. A silk fiber in the form of cylindrical and thin fiber may be obtained by electric spinning.

To the silk fiber obtained by electric spinning, a least one selected from the group consisting of DMSO, $H_2O_2$, calcium phosphate, potassium ferricyanide, and glutaraldehyde may be added as one cross-linking agent in the form of vapor or solution, and thus strength of the silk fiber may be improved.

Further, the recombinant silk protein derived from sea anemones may be mixed with a polymer compound, followed by performing electric spinning. Examples of the polymer compound include poly-ethylene oxide (PEO), polydioxanone (PDO), polycaprolactone (PCL), poly-lactic-co-glycolic acid (PLGA), poly-L-lactide acid (PLLA), chitosan, collagen, or the like, but are not limited thereto.

As described above, the recombinant silk protein derived from sea anemone according to the present invention has sequence features similar to genetic information of a silk protein derived from spiders and silkworms, and is present in external surface tissues and tentacles of sea anemones. This is found by immunohistochemistry using *Nematostella vectensis* species. With respect to recombinant protein, a large amount of the recombinant silk protein derived from sea anemones may be produced from the transformant and it may have good physical properties such as strength and elasticity. Therefore, according to the present invention, the recombinant silk protein derived from sea anemones can be usefully applied in various industrial fields in which natural silk protein can be applied, and it is expected to create new industrial fields based on its distinctive mechanical properties.

Hereinafter, preferable Examples will be described in order to facilitate a comprehensive understanding of the present invention. However, the following Examples do not limit the scope of the present invention.

EXAMPLE 1

Preparation of Expression Vector of Sea Anemone Silk Protein

1. Optimization of DNA Sequence of Sea Anemone Silk Protein

The sea anemone silk protein used in the experiment was hypothetical protein which is set out in information of NCBI Reference Sequence (XP_001621085.1).

The sea anemone silk protein is formed of 319 amino acids which mainly include glycine (35%) and proline (18%), has a specific structure sequence in which ten amino acids (GPGNTGYPGQ; SEQ ID NO: 4) are repeated 30 times and one or two amino acids may be different in the middle or in front of the sequence [repeated sequence of the sea anemone silk protein (including modified sequence)—(G/D)(P/S)(G/S)NTG(Y/C)P(G/W)Q; mainly GPGNTGYPGQ, DPGNTGYPGQ, GPSNTGYPWQ, or the like—SEQ ID NO. 4]. Since DNA sequences to be repeated in the same amino acid sequence may be easily removed from *E-coli*, in order to prevent repetition of the sequence at the DNA level and to facilitate expression of protein, a portion of a codon sequence in an mRNA sequence of the sea anemone silk protein was rearranged so as to be optimized.

Further, a transcription-controlling sequence was significantly affected to form a secondary structure of a transferred substance, by which stop and lasting of transcription are affected. Thus, a portion of the repeated sequence in which a secondary structure is hardly formed was arranged in front of the sea anemone silk protein to reduce the problems.

The amino acid sequence of the natural sea anemone silk protein (theoretical pI: 3.98, theoretical molecular weight: 29.35 kDa) is shown as SEQ ID NO.1.

2. Preparation of Expression Vector of Sea Anemone Silk Protein

DNA of the optimized sea anemone silk protein described in "1. Optimization of DNA sequence of sea anemone silk protein" was added to restriction enzyme sites, Nde1 and Xho1 at both ends, followed by cloning into an expression vector, pET23b (+). The pET23b (+) vector was allowed to include a histidine tag [6×his purification tag sequence; HHHHHH—SEQ ID NO. 5] at C-terminal. Further, a TrpL motif was connected to N-terminal of the sea anemone silk protein using enterokinase cleavage, in order to increase the amount of the sea anemone silk protein to be expressed [expression-enhanced motif sequence; MKAIFVLKDDDDK—SEQ ID NO. 6]. The prepared expression vector included an *E-coli* expression promoter T7 (pT7)

Figure 2:
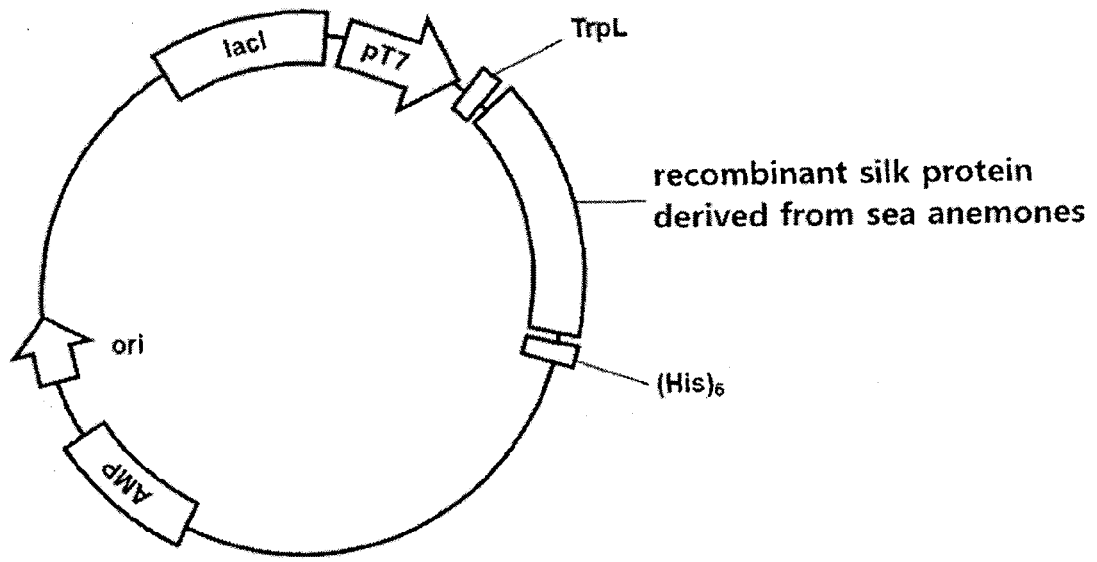
FIG. 2 is a schematic diagram of an expression vector including genes of a sea anemone silk protein (30 kDa) with an expression-enhanced motif.

The schematic diagram of expression vector including genes of the sea anemone silk protein is shown in FIG. 1, and the schematic diagram of expression vector including genes of the sea anemone silk protein with an expression-enhanced motif is shown in FIG. 2.

In a case of the expression vector to make a protein having a size of 60 kDa by increasing repetition sequences, a fragment in which a target protein was located among two fragments obtained by processing Bgl1 and Sal1 in the expression vector (FIGS. 1 and 2) was bonded to a fragment in which a target protein was located among two fragments obtained by processing Bgl1 and Xho1 in the expression vector (FIGS. 1 and 2) to make an expression vector. The schematic diagram of an expression vector of the genes of sea anemone silk protein coding silk proteins having sizes of 60 kDa, 90 kDa, and 120 kDa produced by repeating genes of a sea anemone silk protein twice, three times, and four times is shown in FIG. 3.

EXAMPLE 2

Preparation of Transformed *E-coli* Producing Recombinant Silk Protein Derived from Sea Anemones Conventionally, *E-coli*, TOP10 (Invitrogen) which was mainly used for cloning, and *E-coli*, BL21 (DE3) which was used for protein expression, were made into reactive cells using a $CaCl_2$ buffer. Subsequently, the expression vector prepared in Example 1 was inserted in *E-coli* by a thermal shocking method of standing for 2 minutes at 42° C. to prepare transformed *E-coli*.

EXAMPLE 3

Expression and Purification of Recombinant Silk Protein Derived from Sea Anemones 1. Expression of Recombinant Silk Protein Derived from Sea Anemones The transformed *E-coli* in Example 2 was inoculated onto an LB medium containing 50 mg/mL of ampicillin, followed by shaking for 10 minutes at 37° C. in a 5 L incubator. In order to induce expression of the recombinant silk protein derived from sea anemones, when the ($OD_{600}$) absorbance of a culture medium was 0.8 to 0.9 at 600 nm, an inducing material, isopropyl-β-D-thiogalactopyranoside (IPTG) was added thereto. The cultured cells were centrifuged for 10 minutes at 4000 rpm to remove a supernatant, and then recovered. The recovered cells were floated in a lysis buffer (pH 8.0, 50 mM $NaH_2PO_4$, 300 mM NaCl, 10 mM imidazole) and then broken using a sonicator or a homogenizer. In order to identify expression of the recombinant silk protein derived from sea anemones by SDS-PAGE, a portion of the broken cells were separated into a whole cell lysate, a soluble fraction, and an insoluble fraction. The remaining whole cell lysate was centrifuged for 15 minutes at 9000 rpm to recover a supernatant.

2. Purification of Recombinant Silk Protein Derived from Sea Anemones 2-1. Purification Method Using his-Tag Column The expressed silk protein derived from sea anemones expressed in the soluble fraction was separated and purified from the recovered supernatant using a his-tag column. Preferably, protein of the soluble fragment was injected into a nickel-nitrilotriacetic acid (NTA) column, followed by storing long enough that the protein bonded to the column. Subsequently, protein which did not bond to the column was washed using a washing solution (50 mM $NaH_2PO_4$, 300 mM NaCl, 30 mM imidazol, pH 8.0), and the protein was separated and purified from the column using an elution buffer (50 mM $NaH_2PO_4$, 300 mM NaCl, 300 mM imidazol, pH 8.0).

2.2. Purification Method by Thermal Shocking and Acid Extraction

The recombinant silk protein derived from sea anemones could be purified by thermal shocking and acid extraction as another method of separation and purification. Specifically, the soluble fragment was recovered in the broken cells, and subjected to thermal shocking at around 42° C. At this time, the formed insoluble fragment was separated by centrifugation, and the separated insoluble fragment was sufficiently dissolved in a phosphoric acid. The solution was centrifuged again to obtain a supernatant, the protein completely dissolved in acid was separated from the supernatant, and then components other than water and protein in an aqueous protein solution were removed through dialysis using water for one day. The dialyzed protein was subjected to freeze-drying to obtain a powdery, recombinant silk protein derived from sea anemones.

The amino acid sequence of the recombinant silk protein derived from sea anemones produced from the transformed *E-coli* (theoretical pI: 5.28, theoretical molecular weight: 30.49 kDa) and the amino acid sequence of the recombinant silk protein derived from sea anemones with an expression-enhanced motif (theoretical pI: 5.11, theoretical molecular weight: 31.88 kDa) are shown as SEQ ID Nos. 2 and 3, respectively.

EXAMPLE 4

Identification of Purified Recombinant Silk Protein Derived from Sea Anemones

1. Identification of Purified Recombinant Silk Protein Derived from Sea Anemones Using SDS-PAGE and Western Blot Respective fragments and the purified sample obtained in Example 3 were diluted in a SDS-PAGE buffer (0.5M Tris-HCl (pH 6.8), 10% glycerol, 5% SDS, 5% β-mercaptoethanol, 0.25% bromophenol blue), boiled and denatured for 5 minutes at 100° C. The sample was separated according to molecular weight by SDS-PAGE in 12% SDS-polyacrylamide gel. Further, expression of recombinant silk protein derived from sea anemones was identified through western blot.

Figure 4:
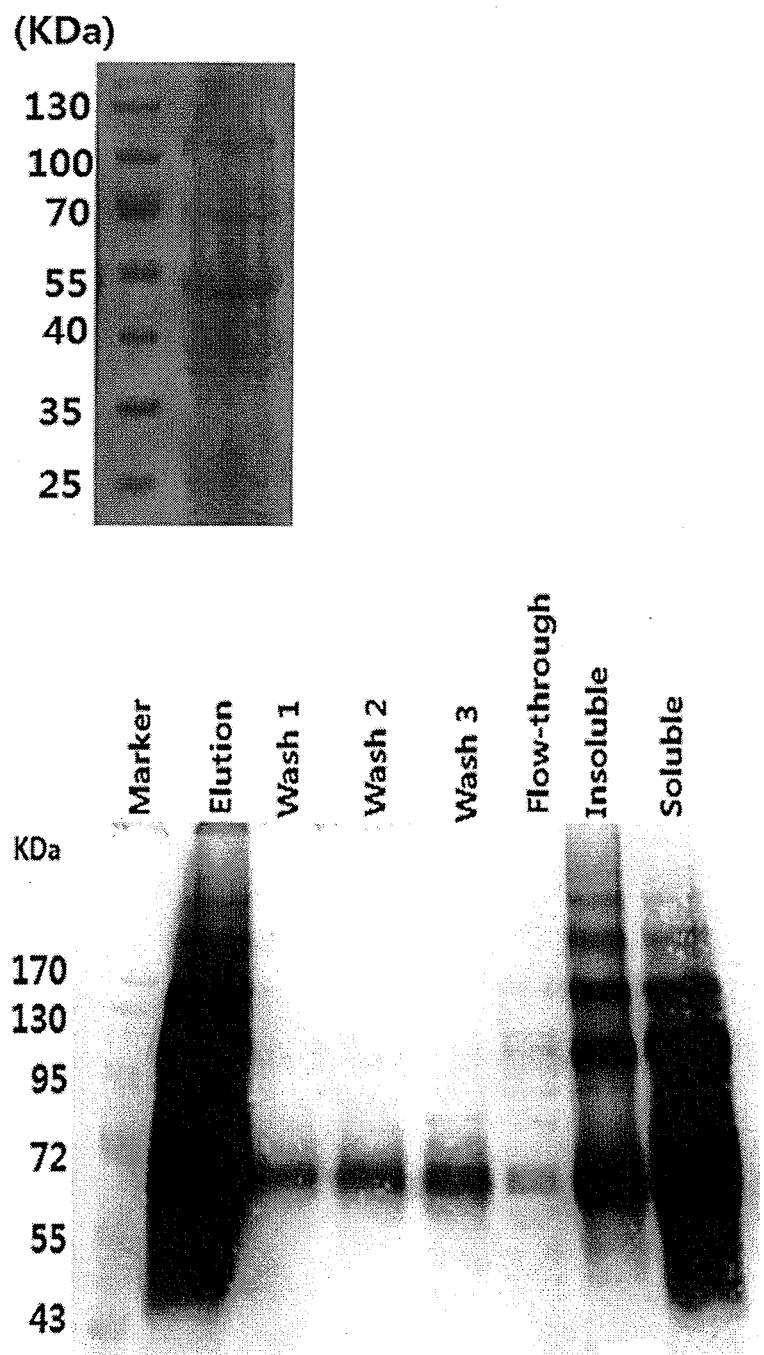
FIG. 4 shows expression of a recombinant silk protein derived from sea anemones identified by SDS-PAGE and western blot.
Figure 5:
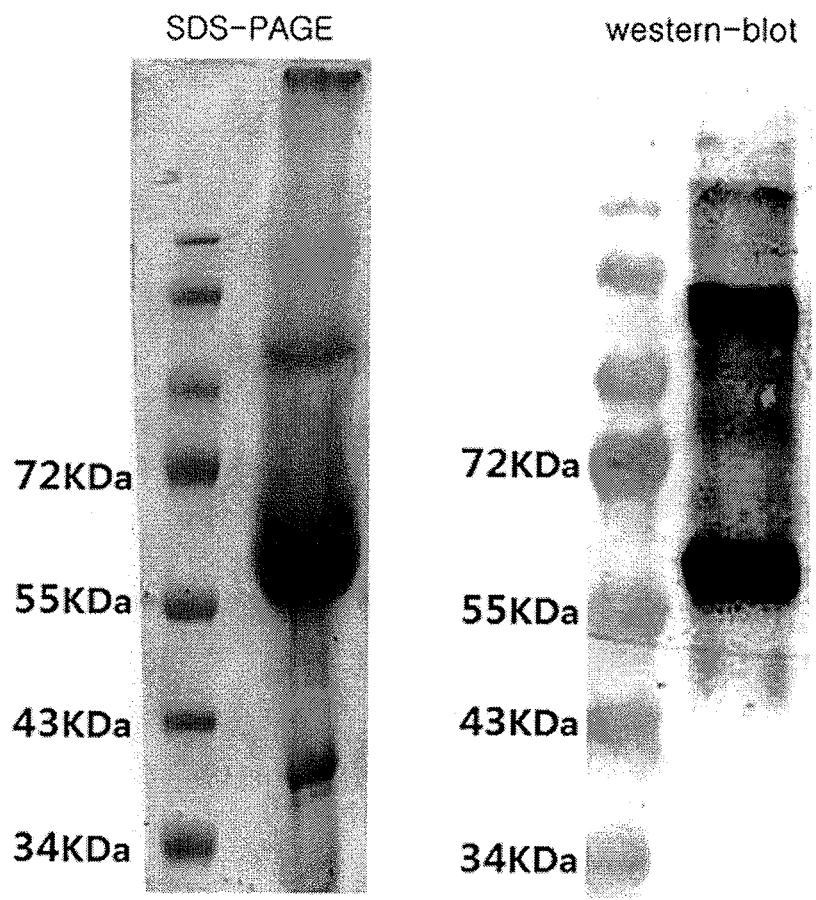
FIG. 5 shows expression of a recombinant silk protein derived from sea anemones with an expression-enhanced motif identified by SDS-PAGE and western blot.
Figure 6:
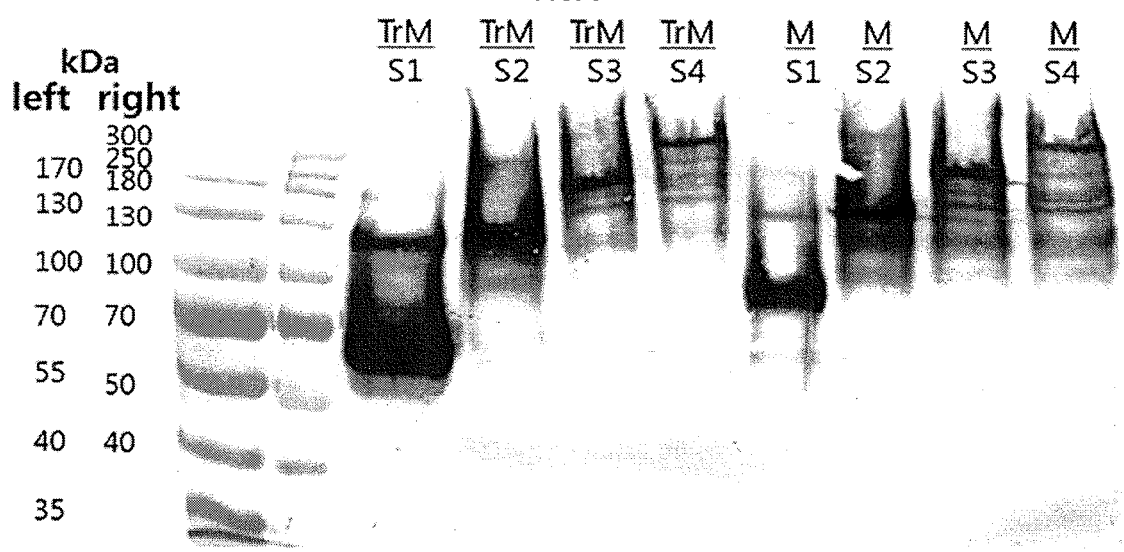
FIG. 6 shows expression of a recombinant silk protein derived from sea anemones having sizes of 30 kDa, 60 kDa (repeated twice), 90 kDa (repeated three times), and 120 kDa (repeated four times) with or without a motif, identified by a western blot, TrM: recombinant silk protein derived from sea anemones with a motif, M: recombinant silk protein derived from sea anemones without a motif, S1: silk protein derived from sea anemones having a size of 30 kDa, S2: silk protein derived from sea anemones having a size of 60 kDa (repeated twice), S3: silk protein derived from sea anemones having a size of 90 kDa (repeated three times), S4: silk protein derived from sea anemones having a size of 120 kDa (repeated four times)

Expression of a recombinant silk protein derived from sea anemones identified by SDS-PAGE and western blot is shown in FIG. 4, and expression of a recombinant silk protein derived from sea anemones with an expression-enhanced motif identified by SDS-PAGE and western blot is shown in FIG. 5.

As shown in FIGS. 4 and 5, whereas the sea anemone silk protein had a size of about 30 kDa, the recombinant silk protein derived from sea anemones included a large amount of proteins found at a position of not 30 kDa but 60 kDa or more when it was subjected to SDS-PAGE. It is thought that particles hardly moved at the time of SDS-PAGE due to sequence features of an amino acid of the recombinant silk protein derived from sea anemones. The phenomenon occurred in silk proteins having sizes of 60 kDa, 90 kDa, and 120 kDa produced by repeating genes of a sea anemone silk protein twice, three times, and four times, which is shown in FIG. 5.

2. Mass Spectrometry of Purified Recombinant Silk Protein Derived from Sea Anemones It is difficult to measure the correct size of the recombinant silk protein derived from sea anemones by SDS-PAGE, and therefore, the recombinant silk protein derived from sea anemones was subjected to MALDI-MS analysis in order to measure its correct size. Concentration and desalination were carried out using C4 Ziptip in a-cyano-4-hydroxycinnamic acid (7 mg/1 mL: 50% ACN, 50% D.W., 0.1% TFA as a matrix. Subsequently, about 0.7 to 1.0 μL of the recombinant silk protein derived from sea anemones was eluted from the matrix. A result was derived for a linear mode.

Figure 8:
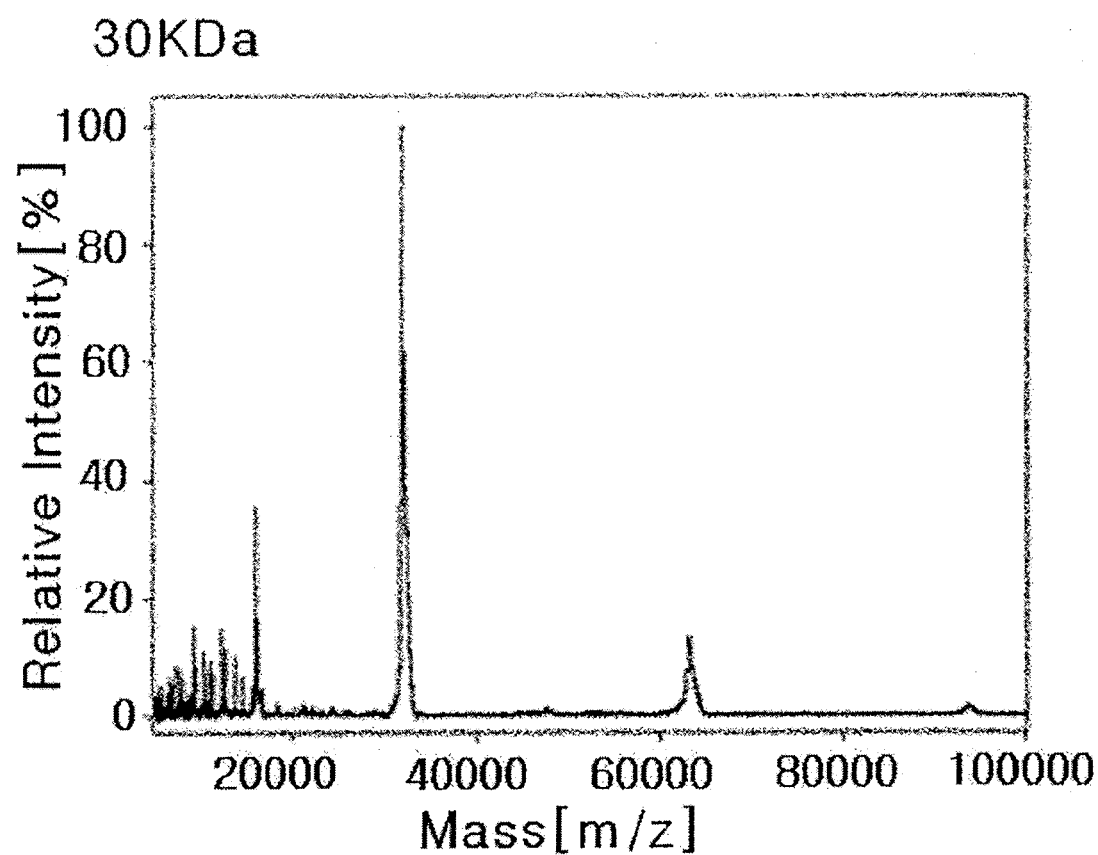
FIG. 8 shows a mass analysis result of a recombinant silk protein derived from sea anemones with an expression-enhanced motif, obtained using MALDI-MS analysis.

A mass analysis of recombinant silk protein derived from sea anemones, and a mass analysis of recombinant silk protein derived from sea anemones with an expression-enhanced motif, obtained using MALDI-MS analysis, are shown in FIGS. 7 and 8, respectively.

As shown in FIGS. 7 and 8, it was found that mass of the recombinant silk protein derived from sea anemones and mass of the recombinant silk protein derived from sea anemones with an expression-enhanced motif were present at around 30 kDa.

3. Composition Analysis of Amino Acid of Purified Recombinant Silk Protein Derived from Sea Anemones In order to identify purification of the recombinant silk protein derived from sea anemones, composition analysis of amino acids of the purified recombinant silk protein derived from sea anemones was carried out.

Specifically, the purified recombinant silk protein derived from sea anemones was dissolved in distilled water and subjected to composition analysis of amino acids using an amino acid quantitative analysis kit (amino acid standard H, Pierce Chem. Co.).

Figure 9:
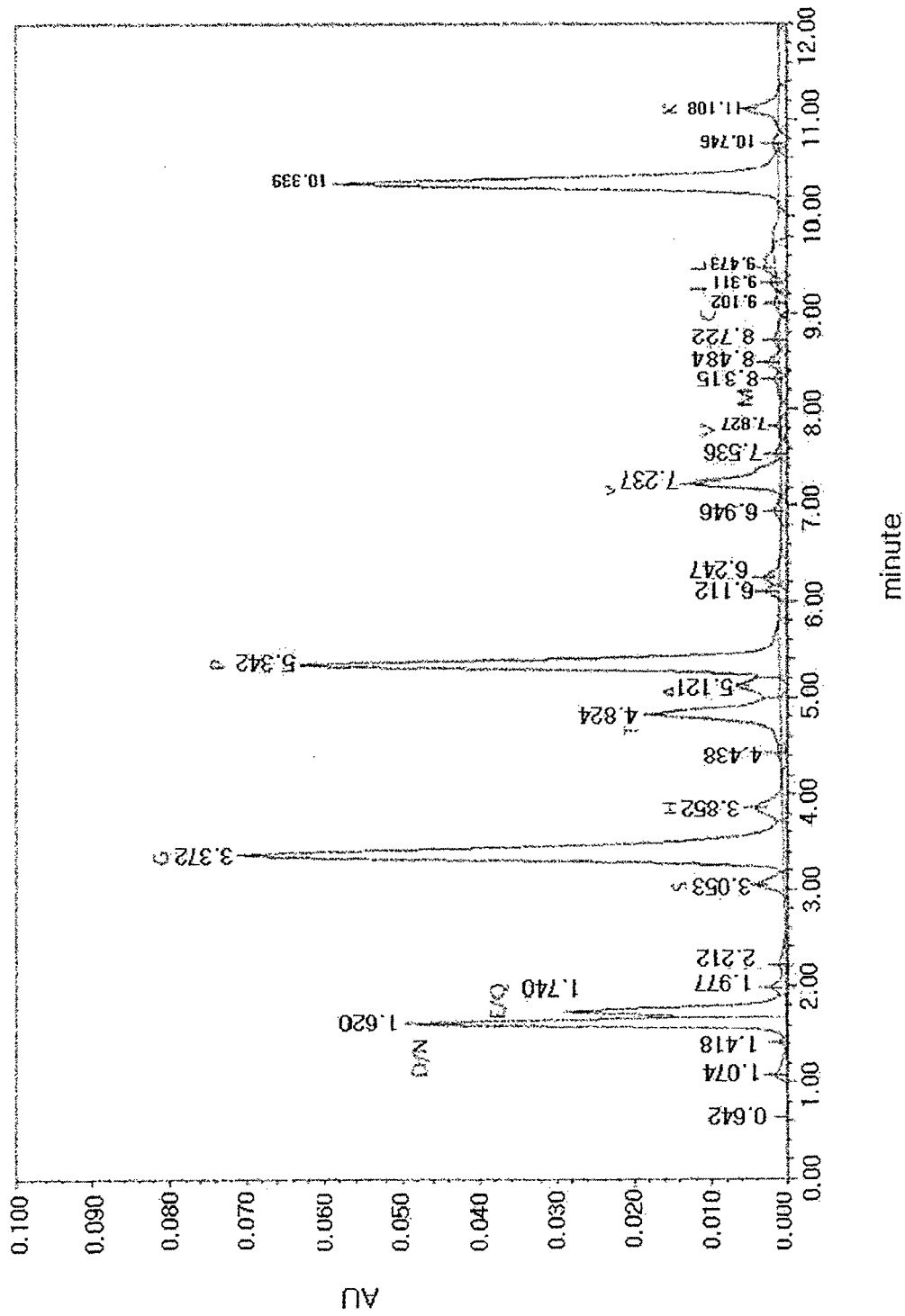
FIG. 9 shows a composition of amino acids of a recombinant silk protein derived from sea anemones with an expression-enhanced motif.

A composition analysis of amino acids of recombinant silk protein derived from sea anemones with an expression-enhanced motif is shown in FIG. 9, and measurement values and theoretical values were compared with respect to a composition analysis of amino acids of the recombinant silk protein derived from sea anemones, which is shown in Table 1.

TABLE 1

|   | Measurement values | Theoretical values |
|---|---|---|
| G | 31.7 | 34.7 |
| P | 17.6 | 17.6 |
| D/N | 17.2 | 12.6 |
| E/Q | 8.4 | 9.7 |
| T | 12.3 | 9.4 |
| Y | 5 | 5 |
| H | 2.1 | 2.9 |
| C | 0.25 | 2.9 |
| S | 1.8 | 1.8 |
| K | 0.84 | 0.9 |
| L | 0.36 | 0.6 |
| V | 0.19 | 0.3 |
| M | 0.14 | 0.3 |
| I | 0.26 | 0.3 |
| F | — | 0.3 |
| A | 1.8 | 0.3 |
| R | 0 | 0 |

As shown in FIG. 9 and Table 1, it was found that separation and purification of the recombinant silk protein derived from sea anemones with an expression-enhanced motif were carried out, and then 19 amino acids were analyzed except for tryptopan.

EXAMPLE 5

Wet Spinning of Recombinant Silk Protein Derived from Sea Anemones According to Dissolution Solvent and Coagulation-Inducing Solvent 1. Determination of Coagulation-Inducing Solvent The silk protein may coagulate in various ways depending on a solvent or liquid to be wet-spun. Therefore, to obtain a silk protein in the form of yarn, the protein should coagulate rapidly such that the protein does not disperse in a coagulation bath but takes the form of yarn with a certain thickness. Therefore, based on existing experimental data related to solubility of silk protein, solubility of the recombinant silk protein derived from sea anemones was measured in various solvents such as hexafluoroisopropanol (HFIP), buffer A (160 mM urea, 10 mM $NaH_2PO_4$, 1 mM Tris (pH 5), 20 mM NaCl), isopropyl alcohol, acetic acid, water, 8M lithium bromide, or formic acid.

Through experiments it was found that the recombinant silk protein derived from sea anemones had very poor solubility in acetic acid, isopropyl alcohol, and 8M lithium bromide, but very good solubility in HFIP or solvent containing 70% or more HFIP. Therefore, it was found that HFIP was very good from the viewpoint of solubility of protein.

Further, the recombinant silk protein derived from sea anemones dissolved in HFIP was wet-spun in a coagulation bath for wet-spinning, and then the coagulated form of the protein was observed. In other words, when the recombinant silk protein derived from sea anemones dissolved in HFIP was wet-spun in a coagulation bath filled with isopropyl alcohol, the spun protein fiber was thin, flexible, and not hard. However, when the recombinant silk protein derived from sea anemones dissolved in HFIP was wet-spun in a coagulation bath filled with methanol, the spun protein fiber was rough, thick, and took the form of yarn with good hardness for handling. Therefore, the mixed solvent of isopropanol and methanol was optimal as the coagulation-inducing solvent. Depending on surface morphology, thickness, or coagulation of a desirable protein, a solvent of various compositions could be used. In the present invention, the following experiment was carried out using isopropanol and methanol mixed in the same amount.

The recombinant silk protein derived from sea anemones purified using acid extraction also used the aforementioned solvent condition.

2. Wet Spinning of Recombinant Silk Protein Derived from Sea Anemones According to Coagulation-Inducing Solvent Since the recombinant silk protein derived from sea anemones according to the present invention includes a histidine tag, it was subjected to separation and purification using a nickel-nitrilotriacetic acid (NTA) column. The high-purity, recombinant silk protein derived from sea anemones was dissolved in HFIP, and then wet spun at a rate of 10 to 15 mL/hr in a mixed solvent of methanol and isopropanol (mixing at a volume ratio of 1:1) to obtain a protein in the form of yarn having a relatively homogenous diameter. The obtained protein in the form of yarn was kept for 20 to 30 minutes in a mixed coagulation solvent, and then dipped three times in methanol and water at interval of 20 minutes to induce change of physical properties of the protein. Subsequently, the protein in the form of yarn was dried for one day at a condition of 50% humidity. The silk fiber containing the dried recombinant silk protein derived from sea anemones was observed by scanning electron microscope.

Figure 11:
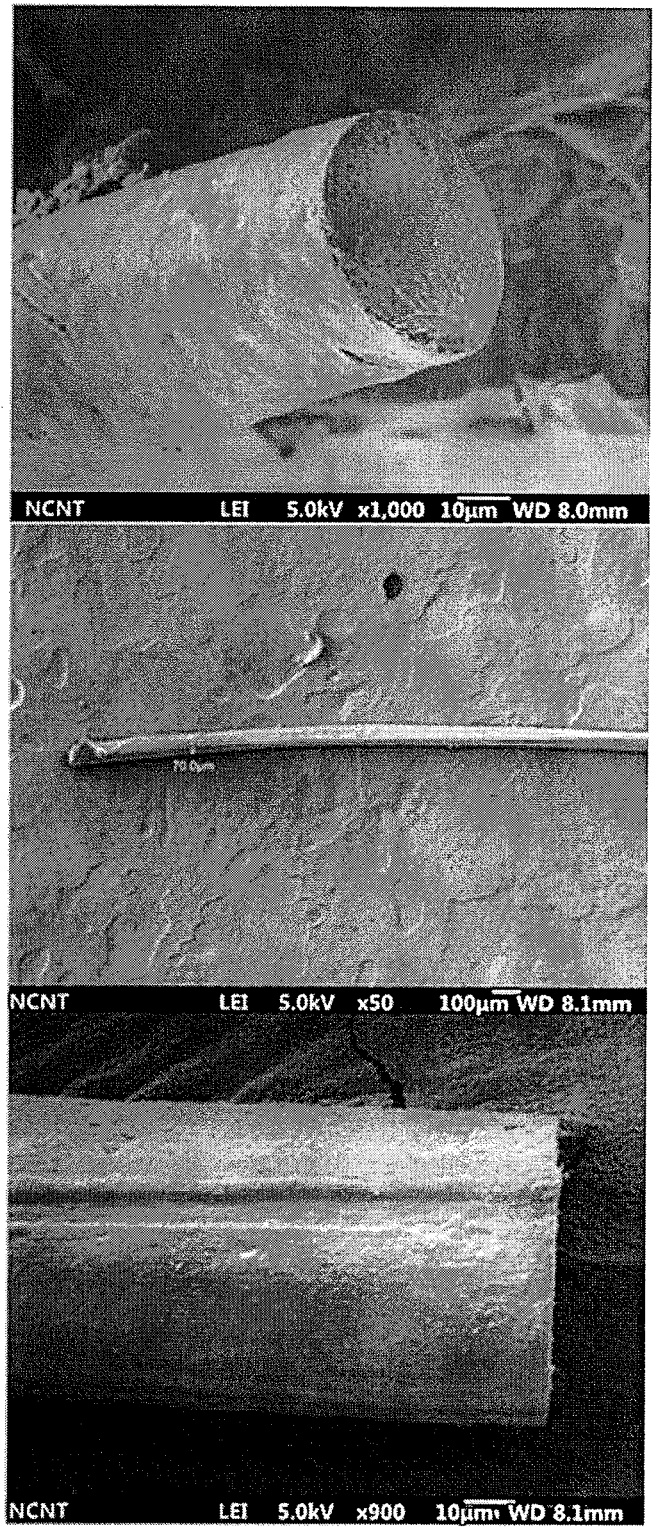
FIG. 11 shows a silk fiber containing a recombinant silk protein derived from sea anemones obtained after wet spinning observed by scanning electron micrograph.
Figure 13:
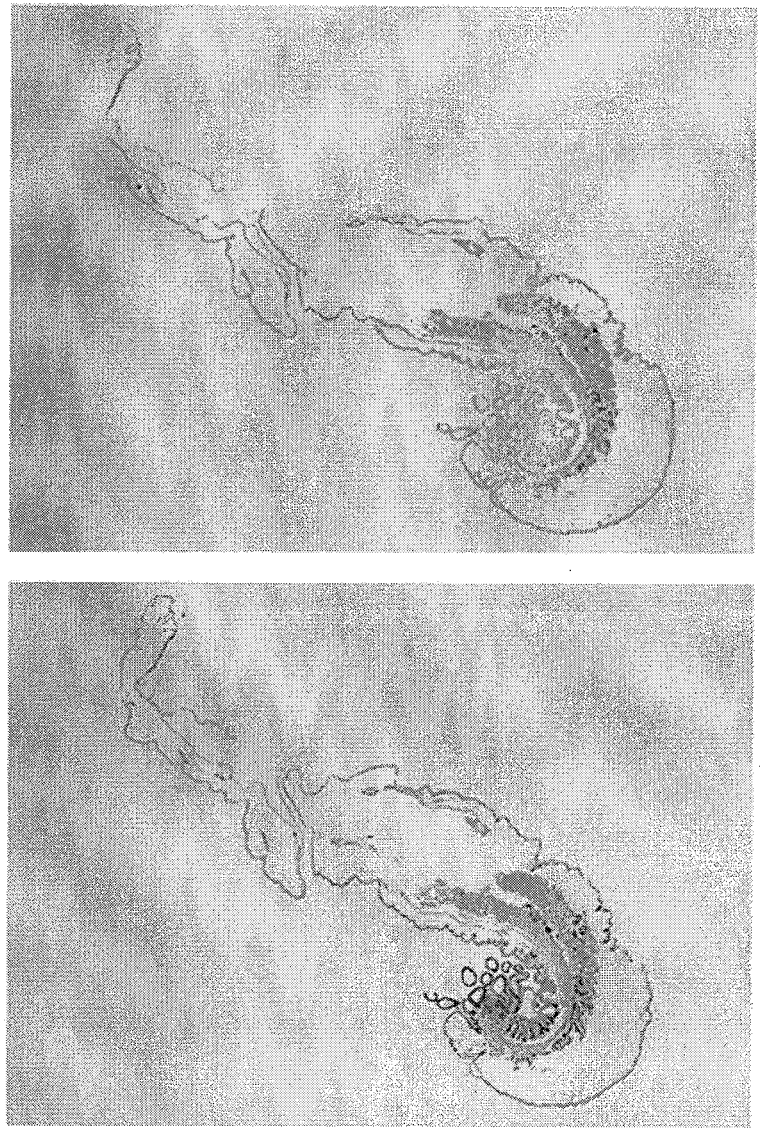
FIG. 13 shows antigen-antibody reaction identified through immunohistochemistry of *Nematostella vectensis*; (a) immunohistochemistry using IgG antibody, (b) immunohistochemistry using an antibody to a silk protein derived from sea anemones.

Aspects and scanning electron microscope images of the silk fibers containing recombinant silk protein derived from sea anemones obtained after wet spinning are shown in FIGS. 10 and 11, respectively.

As shown in FIGS. 10 and 11, it was found that the recombinant silk protein derived from sea anemones obtained after wet-spinning was in the form of yarn with a diameter of 30 to 100 μm. Further, the silk fiber containing recombinant silk protein derived from sea anemones obtained after wet spinning was observed by scanning electron micrograph, and it was found to be in the form of intact and homogeneous yarn.

Figure 16:
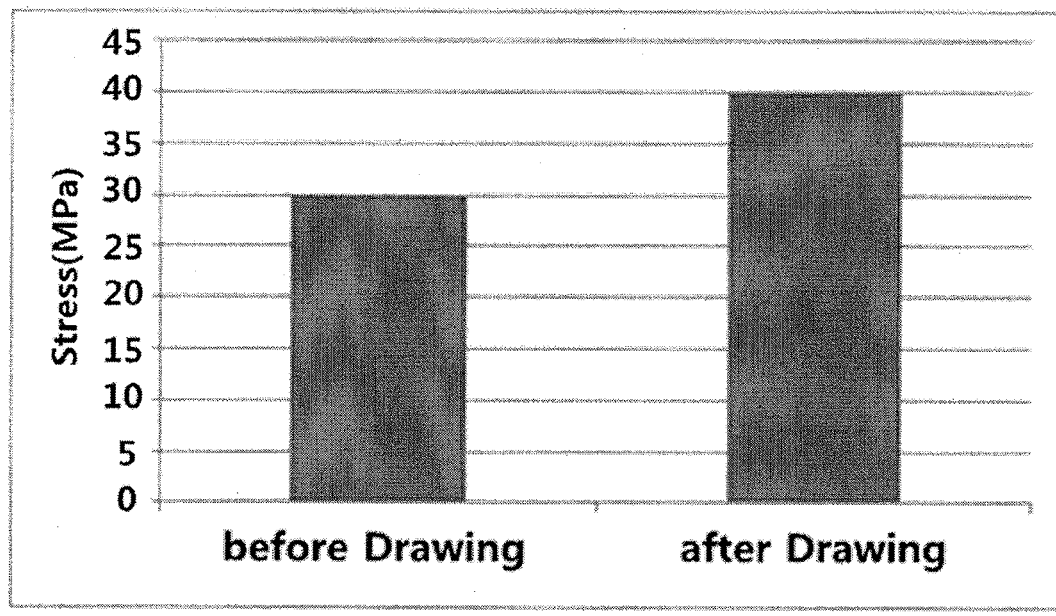
FIG. 16 shows tensile strength after drawing a column purified recombinant silk protein derived from sea anemones having a size of 30 kDa in a dry condition and in an organic solvent used for wet-spinning.

3. Drawing After Wet Spinning of Recombinant Silk Protein Derived from Sea Anemones In a case of the recombinant silk protein derived from sea anemones with an expression-enhanced motif, obtained by a purification method employing thermal shocking and acid extraction, specimens were prepared in a similar manner as in the aforementioned method, except that a first method includes removing the spun fiber protein, followed by drawing to 2-5 times the original length in the air, and a second method includes dipping the fiber protein in the organic solvent used for wet-spinning, followed by drawing to 2-5 times the original length. However, types of organic solvents used for the present invention are not limited. Drawing results are shown in FIG. 16 and physical properties by measurement of tensile strength are shown in Table 2.

EXAMPLE 6

Electric Spinning of Recombinant Silk Protein Derived from Sea Anemones

In the case of the silk protein, the possibility of electric spinning and the shape and thickness of the produced fiber depend on a solvent. Therefore, to obtain a silk protein in the form of yarn through electric spinning, the protein should be completely dissolved with suitable viscosity and electrically spun to a certain thickness without aggregation. The hexafluoroisopropanol (HFIP) used for wet-spinning may satisfactory dissolve the recombinant silk protein derived from sea anemones, but when the dissolved silk protein was electrically spun to form a fiber, and then the fiber was observed by scanning electron microscope, they were wide fibers in the form of ribbons about 1 to 3 μm thick.

Therefore, crude acetic acid corresponding to 10 volume % of the silk protein was added to the recombinant silk protein derived from sea anemones dissolved in HFIP, followed by electric spinning at a voltage of 16 kV, and the silk fiber was observed by scanning electron microscope.

The silk fiber containing the recombinant silk protein derived from sea anemones obtained after electric spinning observed by scanning electron micrograph is shown in FIG. 12.

As shown in FIG. 12, it was found that the recombinant silk protein derived from sea anemones obtained after electric-spinning was formed into a cylindrical, thin fiber with a diameter of at most 0.2 μM (200 nm).

EXAMPLE 7

Figure 14:
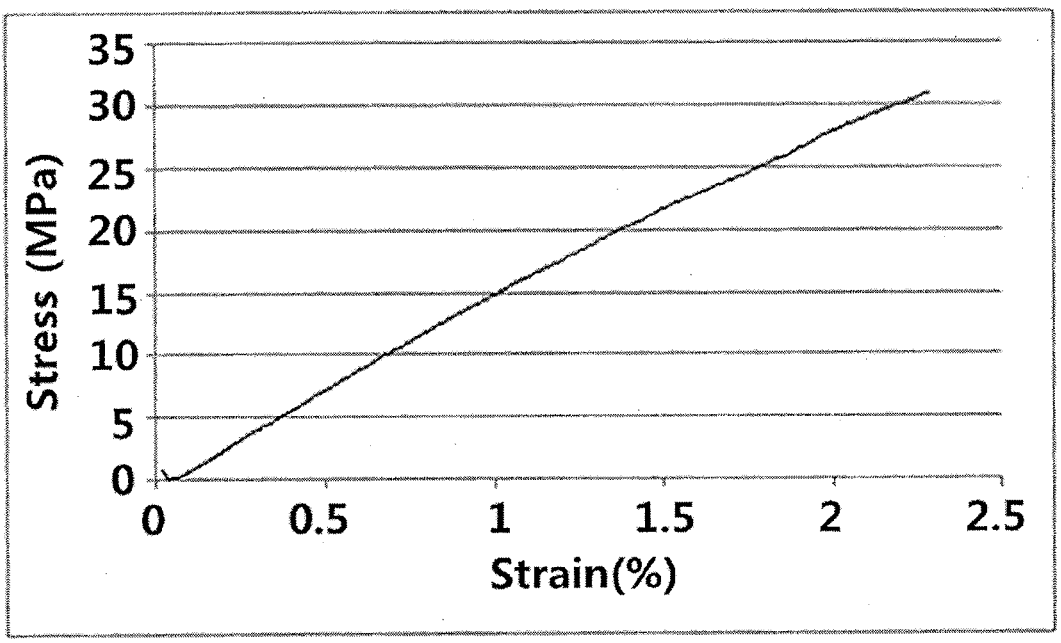
FIG. 14 shows tensile strength of a column purified recombinant silk protein derived from sea anemones having a size of 30 kDa, obtained after wet-spinning.
Figure 15:
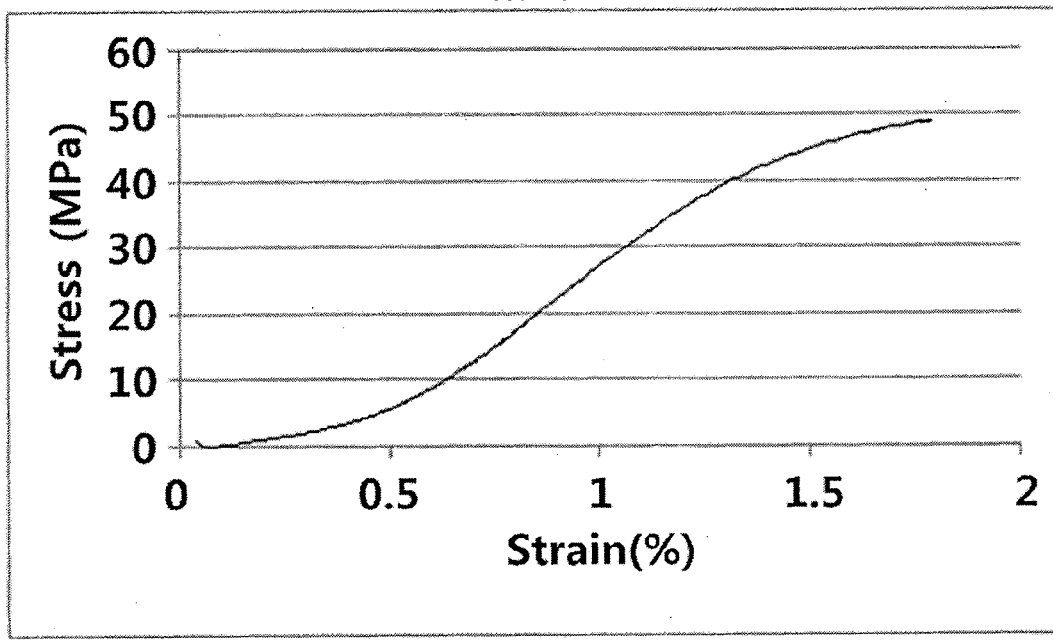
FIG. 15 shows tensile strength of a column purified recombinant silk protein derived from sea anemones having a size of 60 kDa, obtained after wet-spinning.
Figure 17:
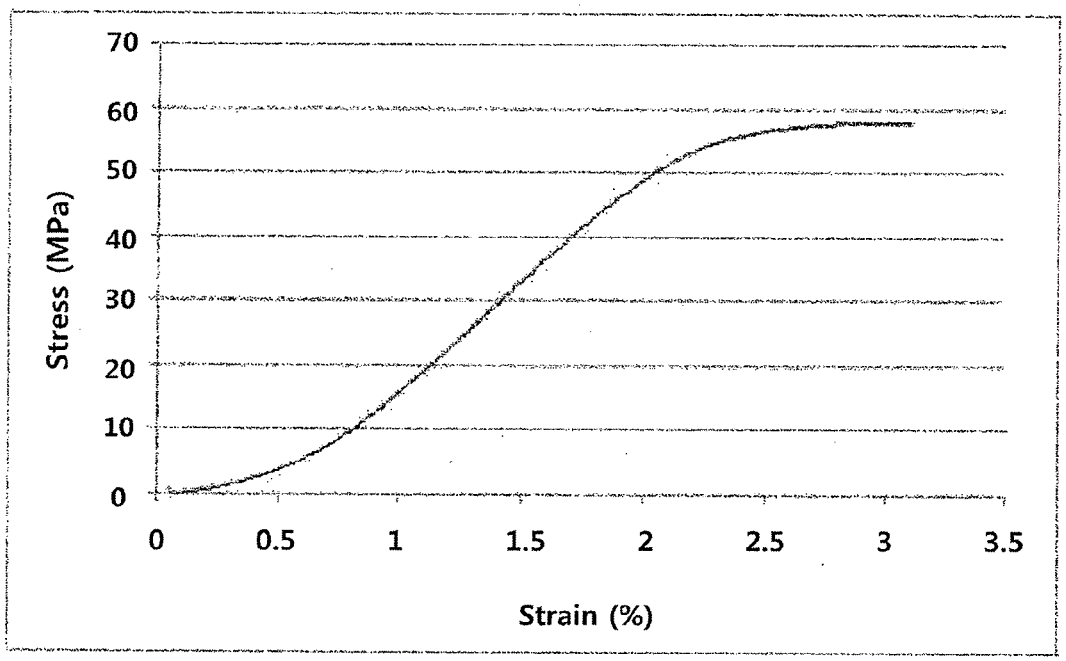
FIG. 17 shows tensile strength of a recombinant silk protein derived from sea anemones having a size of 30 kDa, obtained by a purification method through thermal shocking and acid extraction.
Figure 18:
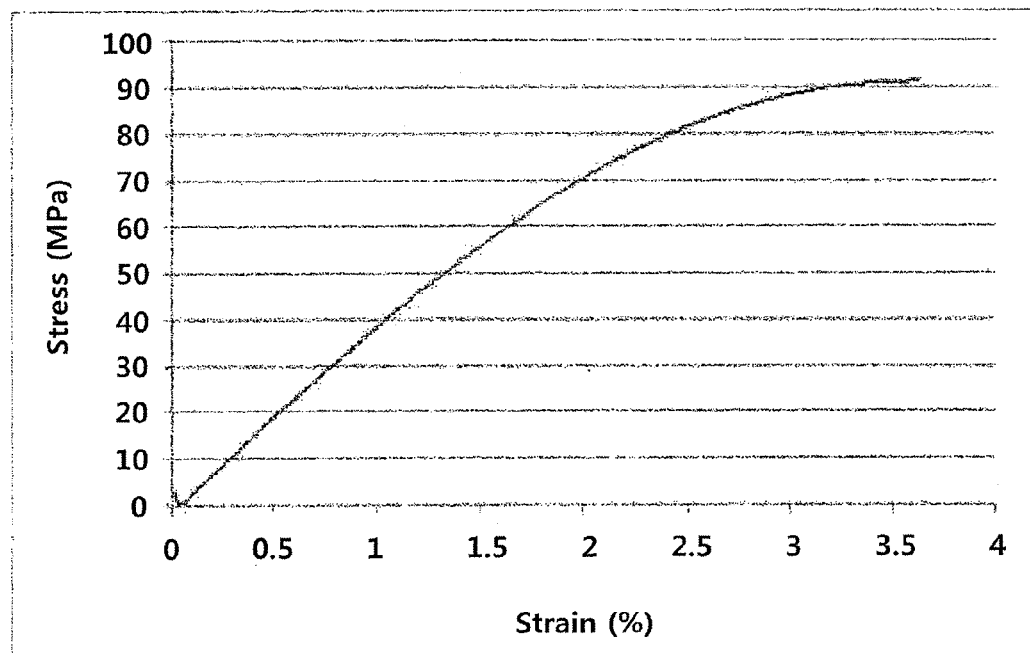
FIG. 18 shows tensile strength test of a recombinant silk protein derived from sea anemones having a size of 60 kDa, obtained by a purification method through thermal shocking and acid extraction.

Measurement of Tensile Strength of Recombinant Silk Protein Derived from Sea Anemones The silk fibers in the form of yarn containing the recombinant silk proteins derived from sea anemones obtained in Examples 5 and 6 were subjected to nano Universal Testing Machine (UTM) experiment to measure their tensile strength, through which stress-strain curves were obtained. Further, physical properties such as strength, elasticity, stiffness, and toughness were measured through this experiment. Respective tensile strengths of the silk fibers including the recombinant silk protein derived from sea anemones obtained after wet-spinning are shown in FIGS. 14 and 15. Respective tensile strengths after wet or dry drawing the recombinant silk protein derived from sea anemones with an expression-enhanced motif, obtained by a purification method employing thermal shocking and acid extraction are shown in FIGS. 17 and 18, respectively. Measurement values of the tensile strength are shown in Table 2.

Physical properties of the fiber were found by the stress-strain curve obtained by analysis of tensile strength. When the fibers were drawn from both ends until they broke, "strain" refers to elasticity and "stress" refers to strength. Toughness is energy required to break the fiber and corresponds to a lower area of the graph. Stiffness is an initial slope of the graph. calculated values are shown in Table 2.

TABLE 2

|  |  | Strength (MPa) | Extensibility (%) | Stiffness (GPa) | Toughness (MJ/M$^3$) |
|---|---|---|---|---|---|
| Colume purified (without motif) | 30 KDa | 29.59 (±5.83) | 2.20 (±0.39) | 1.39 (±0.40) | 0.32 (±0.08) |
|  | 60 KDa | 47.8 (±9.97) | 1.84 (±0.36) | 2.75 (±0.93) | 0.43 (±0.23) |
| Colume purified (with motif) | 30 KDa | 11.21 (±1.42) | 1.47 (±0.18) | 0.96 (±0.19) | 0.07 (±0.04) |
| Heat and Acid purified protein | Wet drawing | 51.95 (±5.98) | 2.71 (±0.58) | 2.21 (±0.43) | 0.74 (±0.31) |
|  | Dry drawing | 62.15 (±11.28) | 4.3 (±2.01) | 2.22 (±0.43) | 1.52 (±0.61) |
| Heat and Acid purified(without motif) | 30 KDa | 53.37 (±7.77) | 2.39 (±0.41) | 2.88 (±0.36) | 0.82 (±0.35) |
|  | 60 KDa | 98.29 (±14.14) | 3.63 (±0.68) | 2.75 (±0.46) | 1.81 (±0.53) |
| Heat and Acid purified(with motif) | 30 KDa | 73.04 (±14.92) | 3.83 (±0.83) | 2.46 (±0.57) | 1.37 (±0.33) |
|  | 60 KDa | 169.46 (±54.57) | 3.35 (±0.60) | 5.03 (±1.13) | 2.94 (±1.24) |

The recombinant silk protein derived from sea anemones according to the present invention has sequence features similar to genetic information of silk proteins derived from spiders and silkworms, and a large amount of recombinant silk protein derived from sea anemones may be produced from transformants and has good physical properties such as strength and elasticity. Therefore, According to the present invention, the recombinant silk protein derived from sea anemones can be usefully applied in various industrial fields in which natural silk protein can be applied, and it is expected to create new industrial fields based on its distinctive mechanical properties.

According to the present invention, the recombinant silk protein derived from sea anemones can be usefully applied in various industrial fields in which natural silk protein can be applied, and it is expected to create new industrial fields based on its distinctive mechanical properties.

```
Sequence list
SEQ. ID. NO. 1(sea anemone):
GPGNTGYPGQ GPGNTGHPGQ GPGNTGYPGQ DPGNTGYPGQ
DPGNTGYPGQ DPGNTGYPGQ GPGNTGCPGQ GPGNTGCPGQ
GPGNTGYPGQ GPGNTGYPGQ GPSNTGYPWQ GPGNTGPGNT
GYPGQGPGNT GHPGQGPGNT GYPGQDPGNT GYPGQDPGNT
GCPGQGPGNT GCPGQGSGNT GCPGQGSGNT GCPGQGPGQG
PGNTGYPGQG PGNTGHPGQG PGNTGYPGQD PGNTGYPGQD
PGNTGCPGQG PGNTGCPGQG SGNTGCPGQG SGNTGCPGQG
PGQGPGNTGY PGQGPGNTGY PGQGPGNTGY PGQGPGNTG
```

SEQ. ID. NO. 2(sea anemone):
MGPGNTGYPG QGPGNTGHPG QGPGNTGYPG QDPGNTGYPG
QDPGNTGYPG QDPGNTGYPG QGPGNTGCPG QGPGNTGCPG
QGPGNTGYPG QGPGNTGYPG QGPSNTGYPW QGPGNTGPGN
TGYPGQGPGN TGHPGQGPGN TGYPGQDPGN TGYPGQDPGN
TGCPGQGPGN TGCPGQGSGN TGCPGQGSGN TGCPGQGPGQ
GPGNTGYPGQ GPGNTGHPGQ GPGNTGYPGQ DPGNTGYPGQ
DPGNTGCPGQ GPGNTGCPGQ GSGNTGCPGQ GSGNTGCPGQ
GPGQGPGNTG YPGQGPSNTG YPGQGPGNTG YPGQGPGNTL
EHHHHHH SEQ. ID. NO. 3(sea anemone):
HMKAIFVLKD DDDKGPGNTG YPGQGPGNTG HPGQGPGNTG
YPGQDPGNTG YPGQDPGNTG YPGQDPGNTG YPGQGPGNTG
CPGQGPGNTG CPGQGPGNTG YPGQGPGNTG YPGQGPSNTG
YPWQGPGNTG PGNTGYPGQG PGNTGHPGQG PGNTGYPGQD
PGNTGYPGQD PGNTGCPGQG PGNTGCPGQG SGNTGCPGQG
SGNTGCPGQG PGQGPGNTGY PGQGPGNTGH PGQGPGNTGY
PGQDPGNTGY PGQDPGNTGC PGQGPGNTGC PGQGSGNTGC
PGQGSGNTGC PGQGPGQGPG NTGYPGQGPS NTGYPGQGPG
NTGYPGQGPG NTLEHHHHHH SEQ. ID. NO. 4 (First X is G or D, second X
is P or S, third X is G or S, seventh X is
Y or C, ninth X is G or W.): XXXNTGXPXQ

SEQ. ID. NO. 5: HHHHHH

SEQ ID NO. 6: MKAIFVLKDDDDK

SEQ ID NO. 7: GPGXX (X = A,V,S,Y)

---

What is claimed is:

1. A method of producing a recombinant silk protein, the method comprising:

provinding an expression vector comprising a nucleotide sequence encoding the recombinant silk protein, said recombinant silk protein comprising an amino acid sequence or a sequence homolog with at least 90% homology to the amino acid sequence, wherein the amino acid sequence comprises 2 to 200 repeats of SEQ ID NO: 4 with a C-terminal at one end and an N-terminal at the other end, SEQ ID NO: 5 connected at the C-terminal, and SEQ ID NO: 6 connected at the N-terminal, inserting the expression vector into a host cell to provide a transformant, causing the transformant to produce the recombinant silk protein, and collecting the produced recombinant silk protein comprising the amino acid sequence or a sequence homolog with at least 90% homology to the amino acid sequence.

2. The method of claim 1, wherein the amino acid sequence comprises SEQ ID NO: 3.

3. The method of claim 1, wherein the host cell is at least one selected from the group consisting of *E-coli*, yeast, animal cells, plant cells, and insect cells.

4. A method of producing a silk fiber, the method comprising:

the method of claim 1, and wet-spinning the collected recombinant silk protein.

5. The method of claim 4, wherein the amino acid sequence comprises SEQ ID NO: 3.

6. The method of claim 4, wherein in the wet-spinning, the collected recombinant silk protein is dissolved in at least one solvent selected from the group consisting of phosphoric acid, acetic acid, formic acid, hydrochloric acid, sulfuric acid, nitric acid, hexafluoroisopropanol (HFIP), hexafluoropropanol (HFP), hexafluoroacetone (HFA), trifluoroacetic acid (TFA), and methylimidazolium chloride, or at least one solvent selected from the group consisting of phosphoric acid, acetic acid, formic acid, hydrochloric acid, sulfuric acid, nitric acid, HFIP, HFP, HFA, TFA and methylimidazolium chloride in which at least one selected from the group consisting of urea, LiBr, N-methylmorpholine-N-oxide (NMMO), and zolium chrolide is dissolved, and wherein the recombinant silk protein is wet-spun at a rate of 0.5 to 20 mL/hr in at least one coagulation-inducing solvent selected from the group consisting of methanol, isopropanol, acetone, ammonium sulfate, and water.

7. The method of claim 4, further comprising drawing the spun recombinant silk protein.

8. A method of producing a silk fiber, the method comprising:

the method of claim 1, and electric-spinning the collected recombinant silk protein.

9. The method of claim 8, wherein the amino acid sequence comprises SEQ ID NO: 3.

10. The method of claim 8, wherein in the electric-spinning, the purified recombinant silk protein is dissolved in at least one solvent selected from the group consisting of phosphoric acid, acetic acid, formic acid, hydrochloric acid, sulfuric acid, nitric acid, hexafluoroisopropanol (HFIP), hexafluoropropanol (HFP), hexafluoroacetone (HFA), trifluoroacetic acid (TFA), and methylimidazolium chloride, or at least one solvent selected from the group consisting of phosphoric acid, acetic acid, formic acid, hydrochloric acid, sulfuric acid, nitric acid, HFIP, HFP, HFA, TFA, and methylimidazolium chloride in which at least one selected from the group consisting of urea, LiBr, N-methylmorpholine-N-oxide (NMMO), and zolium chrolide is dissolved, and wherein acetic acid is added to the recombinant silk protein solution to provide a mixture, and the mixture is electrically spun at a voltage of 10 to 20 kV.

* * * * *

SEQUENCE LISTING

<160> NUMBER OF SEQ ID NOS: 7

<210> SEQ ID NO 1
<211> LENGTH: 319
<212> TYPE: PRT
<213> ORGANISM: sea anemone

<400> SEQUENCE: 1

Gly Pro Gly Asn Thr Gly Tyr Pro Gly Gln Gly Pro Gly Asn Thr Gly
1               5                   10                  15

His Pro Gly Gln Gly Pro Gly Asn Thr Gly Tyr Pro Gly Gln Asp Pro
            20                  25                  30

Gly Asn Thr Gly Tyr Pro Gly Gln Asp Pro Gly Asn Thr Gly Tyr Pro
        35                  40                  45

Gly Gln Asp Pro Gly Asn Thr Gly Tyr Pro Gly Gln Gly Pro Gly Asn
    50                  55                  60

Thr Gly Cys Pro Gly Gln Gly Pro Gly Asn Thr Gly Cys Pro Gly Gln
65                  70                  75                  80

Gly Pro Gly Asn Thr Gly Tyr Pro Gly Gln Gly Pro Gly Asn Thr Gly
                85                  90                  95

Tyr Pro Gly Gln Gly Pro Ser Asn Thr Gly Tyr Pro Trp Gln Gly Pro
            100                 105                 110

Gly Asn Thr Gly Pro Gly Asn Thr Gly Tyr Pro Gly Gln Gly Pro Gly
        115                 120                 125

Asn Thr Gly His Pro Gly Gln Gly Pro Gly Asn Thr Gly Tyr Pro Gly
    130                 135                 140

Gln Asp Pro Gly Asn Thr Gly Tyr Pro Gly Gln Asp Pro Gly Asn Thr
145                 150                 155                 160

Gly Cys Pro Gly Gln Gly Pro Gly Asn Thr Gly Cys Pro Gly Gln Gly
                165                 170                 175

Ser Gly Asn Thr Gly Cys Pro Gly Gln Gly Ser Gly Asn Thr Gly Cys
            180                 185                 190

Pro Gly Gln Gly Pro Gly Gln Gly Pro Gly Asn Thr Gly Tyr Pro Gly
        195                 200                 205

Gln Gly Pro Gly Asn Thr Gly His Pro Gly Gln Gly Pro Gly Asn Thr
    210                 215                 220

Gly Tyr Pro Gly Gln Asp Pro Gly Asn Thr Gly Tyr Pro Gly Gln Asp
225                 230                 235                 240

Pro Gly Asn Thr Gly Cys Pro Gly Gln Gly Pro Gly Asn Thr Gly Cys
                245                 250                 255

Pro Gly Gln Gly Ser Gly Asn Thr Gly Cys Pro Gly Gln Gly Ser Gly

```
                        260                 265                 270
Asn Thr Gly Cys Pro Gly Gln Gly Pro Gly Gln Gly Pro Gly Asn Thr
                275                 280                 285

Gly Tyr Pro Gly Gln Gly Pro Ser Asn Thr Gly Tyr Pro Gly Gln Gly
            290                 295                 300

Pro Gly Asn Thr Gly Tyr Pro Gly Gln Gly Pro Gly Asn Thr Gly
305                 310                 315

<210> SEQ ID NO 2
<211> LENGTH: 327
<212> TYPE: PRT
<213> ORGANISM: sea anemone

<400> SEQUENCE: 2

Met Gly Pro Gly Asn Thr Gly Tyr Pro Gly Gln Gly Pro Gly Asn Thr
 1               5                   10                  15

Gly His Pro Gly Gln Gly Pro Gly Asn Thr Gly Tyr Pro Gly Gln Asp
                20                  25                  30

Pro Gly Asn Thr Gly Tyr Pro Gly Gln Asp Pro Gly Asn Thr Gly Tyr
            35                  40                  45

Pro Gly Gln Asp Pro Gly Asn Thr Gly Tyr Pro Gly Gln Gly Pro Gly
        50                  55                  60

Asn Thr Gly Cys Pro Gly Gln Gly Pro Gly Asn Thr Gly Cys Pro Gly
65                  70                  75                  80

Gln Gly Pro Gly Asn Thr Gly Tyr Pro Gly Gln Gly Pro Gly Asn Thr
                85                  90                  95

Gly Tyr Pro Gly Gln Gly Pro Ser Asn Thr Gly Tyr Pro Trp Gln Gly
            100                 105                 110

Pro Gly Asn Thr Gly Pro Gly Asn Thr Gly Tyr Pro Gly Gln Gly Pro
        115                 120                 125

Gly Asn Thr Gly His Pro Gly Gln Gly Pro Gly Asn Thr Gly Tyr Pro
130                 135                 140

Gly Gln Asp Pro Gly Asn Thr Gly Tyr Pro Gly Gln Asp Pro Gly Asn
145                 150                 155                 160

Thr Gly Cys Pro Gly Gln Gly Pro Gly Asn Thr Gly Cys Pro Gly Gln
                165                 170                 175

Gly Ser Gly Asn Thr Gly Cys Pro Gly Gln Gly Ser Gly Asn Thr Gly
            180                 185                 190

Cys Pro Gly Gln Gly Pro Gly Gln Gly Pro Gly Asn Thr Gly Tyr Pro
        195                 200                 205

Gly Gln Gly Pro Gly Asn Thr Gly His Pro Gly Gln Gly Pro Gly Asn
        210                 215                 220

Thr Gly Tyr Pro Gly Gln Asp Pro Gly Asn Thr Gly Tyr Pro Gly Gln
225                 230                 235                 240

Asp Pro Gly Asn Thr Gly Cys Pro Gly Gln Gly Pro Gly Asn Thr Gly
                245                 250                 255

Cys Pro Gly Gln Gly Ser Gly Asn Thr Gly Cys Pro Gly Gln Gly Ser
            260                 265                 270

Gly Asn Thr Gly Cys Pro Gly Gln Gly Pro Gln Gly Pro Gly Asn
        275                 280                 285

Thr Gly Tyr Pro Gly Gln Gly Pro Ser Asn Thr Gly Tyr Pro Gly Gln
            290                 295                 300

Gly Pro Gly Asn Thr Gly Tyr Pro Gly Gln Gly Pro Gly Asn Thr Leu
305                 310                 315                 320
```

Glu His His His His His
            325

<210> SEQ ID NO 3
<211> LENGTH: 340
<212> TYPE: PRT
<213> ORGANISM: sea anemone

<400> SEQUENCE: 3

His Met Lys Ala Ile Phe Val Leu Lys Asp Asp Asp Lys Gly Pro
  1               5                  10                  15

Gly Asn Thr Gly Tyr Pro Gly Gln Gly Pro Gly Asn Thr Gly His Pro
             20                  25                  30

Gly Gln Gly Pro Gly Asn Thr Gly Tyr Pro Gly Gln Asp Pro Gly Asn
             35                  40                  45

Thr Gly Tyr Pro Gly Gln Asp Pro Gly Asn Thr Gly Tyr Pro Gly Gln
         50                  55                  60

Asp Pro Gly Asn Thr Gly Tyr Pro Gly Gln Gly Pro Gly Asn Thr Gly
 65                  70                  75                  80

Cys Pro Gly Gln Gly Pro Gly Asn Thr Gly Cys Pro Gly Gln Gly Pro
                 85                  90                  95

Gly Asn Thr Gly Tyr Pro Gly Gln Gly Pro Gly Asn Thr Gly Tyr Pro
                100                 105                 110

Gly Gln Gly Pro Ser Asn Thr Gly Tyr Pro Trp Gln Gly Pro Gly Asn
                115                 120                 125

Thr Gly Pro Gly Asn Thr Gly Tyr Pro Gly Gln Gly Pro Gly Asn Thr
            130                 135                 140

Gly His Pro Gly Gln Gly Pro Gly Asn Thr Gly Tyr Pro Gly Gln Asp
145                 150                 155                 160

Pro Gly Asn Thr Gly Tyr Pro Gly Gln Asp Pro Gly Asn Thr Gly Cys
                165                 170                 175

Pro Gly Gln Gly Pro Gly Asn Thr Gly Cys Pro Gly Gln Gly Ser Gly
                180                 185                 190

Asn Thr Gly Cys Pro Gly Gln Gly Ser Gly Asn Thr Gly Cys Pro Gly
            195                 200                 205

Gln Gly Pro Gly Gln Gly Pro Gly Asn Thr Gly Tyr Pro Gly Gln Gly
        210                 215                 220

Pro Gly Asn Thr Gly His Pro Gly Gln Gly Pro Gly Asn Thr Gly Tyr
225                 230                 235                 240

Pro Gly Gln Asp Pro Gly Asn Thr Gly Tyr Pro Gly Gln Asp Pro Gly
                245                 250                 255

Asn Thr Gly Cys Pro Gly Gln Gly Pro Gly Asn Thr Gly Cys Pro Gly
            260                 265                 270

Gln Gly Ser Gly Asn Thr Gly Cys Pro Gly Gln Gly Ser Gly Asn Thr
        275                 280                 285

Gly Cys Pro Gly Gln Gly Pro Gly Gln Gly Pro Gly Asn Thr Gly Tyr
        290                 295                 300

Pro Gly Gln Gly Pro Ser Asn Thr Gly Tyr Pro Gly Gln Gly Pro Gly
305                 310                 315                 320

Asn Thr Gly Tyr Pro Gly Gln Gly Pro Gly Asn Thr Leu Glu His His
                325                 330                 335

His His His His
            340

<210> SEQ ID NO 4

```
<211> LENGTH: 10
<212> TYPE: PRT
<213> ORGANISM: sea anemone
<220> FEATURE:
<221> NAME/KEY: VARIANT
<222> LOCATION: (1)..(1)
<223> OTHER INFORMATION: Xaa is Gly or Asp
<220> FEATURE:
<221> NAME/KEY: VARIANT
<222> LOCATION: (2)..(2)
<223> OTHER INFORMATION: Xaa is Pro or Ser
<220> FEATURE:
<221> NAME/KEY: VARIANT
<222> LOCATION: (3)..(3)
<223> OTHER INFORMATION: Xaa is Gly or Ser
<220> FEATURE:
<221> NAME/KEY: VARIANT
<222> LOCATION: (7)..(7)
<223> OTHER INFORMATION: Xaa is Tyr or Cys
<220> FEATURE:
<221> NAME/KEY: VARIANT
<222> LOCATION: (9)..(9)
<223> OTHER INFORMATION: Xaa is Gly or Trp

<400> SEQUENCE: 4

Xaa Xaa Xaa Asn Thr Gly Xaa Pro Xaa Gln
 1               5                  10

<210> SEQ ID NO 5
<211> LENGTH: 6
<212> TYPE: PRT
<213> ORGANISM: Artificial Sequence
<220> FEATURE:
<223> OTHER INFORMATION: Synthetic peptide

<400> SEQUENCE: 5

His His His His His His
 1               5

<210> SEQ ID NO 6
<211> LENGTH: 13
<212> TYPE: PRT
<213> ORGANISM: Artificial Sequence
<220> FEATURE:
<223> OTHER INFORMATION: Synthetic peptide

<400> SEQUENCE: 6

Met Lys Ala Ile Phe Val Leu Lys Asp Asp Asp Asp Lys
 1               5                  10

<210> SEQ ID NO 7
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (4)..(5)
<223> OTHER INFORMATION: Xaa is Ala, Val, Ser or Tyr.

<400> SEQUENCE: 7

Gly Pro Gly Xaa Xaa
 1               5
```